(12) United States Patent
Feingold et al.

(10) Patent No.: US 12,003,861 B2
(45) Date of Patent: Jun. 4, 2024

(54) SYSTEMS AND METHODS FOR MITIGATING ARTIFACTS IN MEDICAL IMAGING

(71) Applicant: Stryker Corporation, Kalamazoo, MI (US)

(72) Inventors: Benjamin Hyman Feingold, San Francisco, CA (US); Marc André, Spiegel b. Bern (CH); Levey Trac Tran, Denver, CO (US); Rohit Subramanian, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 345 days.

(21) Appl. No.: 17/560,156

(22) Filed: Dec. 22, 2021

(65) Prior Publication Data
US 2022/0210309 A1 Jun. 30, 2022

Related U.S. Application Data

(60) Provisional application No. 63/132,444, filed on Dec. 30, 2020.

(51) Int. Cl.
*H04N 23/72* (2023.01)
*A61B 1/00* (2006.01)
(Continued)

(52) U.S. Cl.
CPC ......... *H04N 23/72* (2023.01); *A61B 1/00009* (2013.01); *A61B 1/005* (2013.01);
(Continued)

(58) Field of Classification Search
CPC ...... H04N 23/72; H04N 23/555; H04N 23/74; H04N 23/75; H04N 25/531;
(Continued)

(56) References Cited

U.S. PATENT DOCUMENTS

| 3,289,957 A | 12/1966 | Hans-Gunter et al. |
| 6,293,911 B1 | 9/2001 | Imaizumi |

(Continued)

FOREIGN PATENT DOCUMENTS

| EP | 3289957 A1 | 3/2018 |
| JP | 2015-530893 A | 10/2015 |

(Continued)

OTHER PUBLICATIONS

Chang et al., U.S. Notice of Allowance and Fee(s) Due mailed Dec. 21, 2022, directed to U.S. Appl. No. 16/745,154; 11 pages.

(Continued)

*Primary Examiner* — Oschta I Montoya
(74) *Attorney, Agent, or Firm* — Morrison & Foerster LLP

(57) ABSTRACT

An exemplary method of imaging tissue of a subject using a rolling shutter imager to provide a video stream comprises: sequentially resetting a plurality of rows of pixels of the rolling shutter imager from a first row to a last row; transitioning a liquid crystal shutter from a closed state to an open state; after the liquid crystal shutter is transitioned into the open state and after resetting the last row, illuminating the tissue of the subject with an illumination light for an illumination period to accumulate charge at the plurality of rows of pixels, and after the illumination period ends, sequentially reading the accumulated charge at the rows of pixels from the first row to the last row; generating an image frame from the sequentially read accumulated charge at the plurality of rows of pixels; and adding the image frame to the video stream.

26 Claims, 12 Drawing Sheets

(51) Int. Cl.
  *A61B 1/005* (2006.01)
  *A61B 1/05* (2006.01)
  *A61B 1/06* (2006.01)
  *A61B 1/04* (2006.01)
  *H04N 23/50* (2023.01)

(52) U.S. Cl.
  CPC .............. *A61B 1/05* (2013.01); *A61B 1/0684* (2013.01); *A61B 1/042* (2013.01); *H04N 23/555* (2023.01)

(58) Field of Classification Search
  CPC ....... A61B 1/00009; A61B 1/005; A61B 1/05; A61B 1/0684; A61B 1/042
  See application file for complete search history.

(56) References Cited

U.S. PATENT DOCUMENTS

| | | | |
|---|---|---|---|
| 7,059,726 | B2 | 6/2006 | Engle |
| 7,179,222 | B2 | 2/2007 | Imaizumi |
| 7,397,509 | B2 | 7/2008 | Krymski |
| 7,479,990 | B2 | 1/2009 | Imaizumi |
| 8,540,626 | B2 | 9/2013 | Seto et al. |
| 8,550,990 | B2 | 10/2013 | Seto et al. |
| 9,060,404 | B2 | 6/2015 | Upton |
| 9,131,861 | B2 | 9/2015 | Ince et al. |
| 9,307,600 | B2 | 4/2016 | Upton |
| 9,531,156 | B2 | 12/2016 | Hoffman et al. |
| 10,624,535 | B2 | 4/2020 | Sakanoue et al. |
| 11,337,593 | B2 | 5/2022 | Tanaka et al. |
| 11,337,595 | B2 | 5/2022 | Ogawa |
| 11,347,189 | B1 | 5/2022 | Herrera et al. |
| 11,446,810 | B1* | 9/2022 | Chua ...................... B25J 19/023 |
| 11,638,517 | B2 | 5/2023 | Chang et al. |
| 2007/0221823 | A1 | 9/2007 | Xu et al. |
| 2010/0286529 | A1 | 11/2010 | Carroll |
| 2012/0013777 | A1 | 1/2012 | Mao et al. |
| 2013/0050456 | A1* | 2/2013 | Sakurai .................. H04N 23/74 348/311 |
| 2013/0208157 | A1 | 8/2013 | Bechtel et al. |
| 2014/0078277 | A1 | 3/2014 | Dai et al. |
| 2014/0203170 | A1 | 7/2014 | Ono et al. |
| 2014/0225998 | A1 | 8/2014 | Dai et al. |
| 2014/0313386 | A1 | 10/2014 | Jiang et al. |
| 2015/0085077 | A1* | 3/2015 | Kim ...................... H04N 13/296 348/46 |
| 2015/0201871 | A1 | 7/2015 | Shiraishi |
| 2015/0216460 | A1 | 8/2015 | Shigeta |
| 2015/0238086 | A1 | 8/2015 | Saito |
| 2016/0374602 | A1 | 12/2016 | Koshiba |
| 2017/0035280 | A1 | 2/2017 | Yang et al. |
| 2019/0324261 | A1* | 10/2019 | Ogawa ............... G02B 23/2415 |
| 2020/0234439 | A1 | 7/2020 | Chang et al. |
| 2020/0404198 | A1* | 12/2020 | Kobayashi ............. H04N 25/75 |
| 2021/0038066 | A1 | 2/2021 | Bos et al. |
| 2022/0322935 | A1* | 10/2022 | Suzuki ................. A61B 3/0008 |
| 2023/0270324 | A1 | 8/2023 | Chang |
| 2023/0320577 | A1 | 10/2023 | Chang |

FOREIGN PATENT DOCUMENTS

| | | |
|---|---|---|
| JP | 2018-202006 A | 12/2018 |
| JP | 2019-191323 A | 10/2019 |
| WO | 2010/059197 A2 | 5/2010 |
| WO | 2014/018936 A2 | 1/2014 |
| WO | 2017/065057 A1 | 4/2017 |
| WO | 2017/221491 A1 | 12/2017 |

OTHER PUBLICATIONS

Chang et al., U.S. Office Action dated Dec. 21, 2023, directed to U.S. Appl. No. 18/310,515; 13 pages.

Chang et al., U.S. Office Action dated Jun. 8, 2022, directed to U.S. Appl. No. 16/745,154; 14 pages.

Chang et al., U.S. Office Action dated Sep. 28, 2023, directed to U.S. Appl. No. 18/310,517; 16 pages.

Chang et al., U.S. Restriction Requirement dated Jan. 10, 2022, directed to U.S. Appl. No. 16/745,154; 9 pages.

International Preliminary Report on Patentability dated Jul. 4, 2023, directed to International Application No. PCT/US2021/073092; 12 pages.

International Preliminary Report on Patentability dated Jun. 16, 2021, directed to International Application No. PCT/US2020/013912; 13 pages.

International Search Report and Written Opinion mailed Jun. 25, 2020, directed to International Application No. PCT/US2020/013912; 19 pages.

International Search Report and Written Opinion mailed May 27, 2022, directed to International Application No. PCT/US2021/073092; 17 pages.

Invitation to Pay Additional Fees and, where Applicable, Protest Fee and Partial Search mailed Apr. 28, 2020, directed to International Application No. PCT/US2020/013912; 13 pages.

Invitation to Pay Additional Fees and, where applicable, Protest Fee mailed Apr. 4, 2022, directed to International Application No. PCT/US2021/073092; 14 pages.

Notice of Reasons for Refusal dated Nov. 10, 2023, directed to JP Application No. 2021-541534; 6 pages.

* cited by examiner

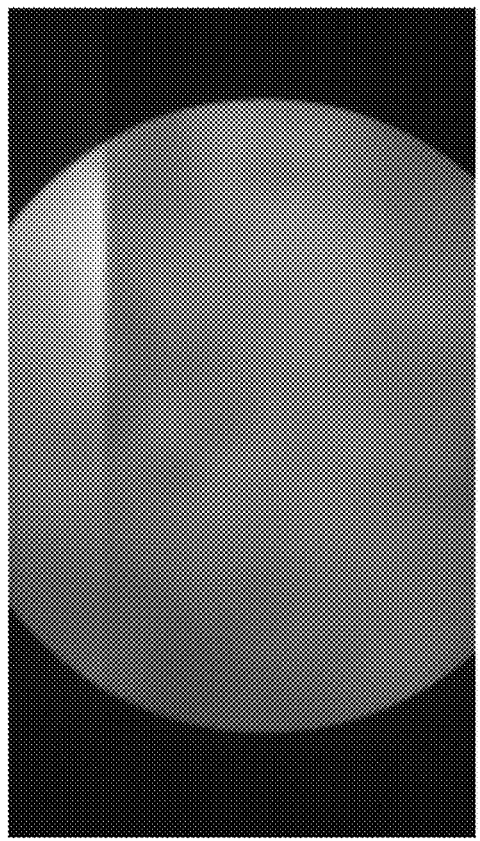
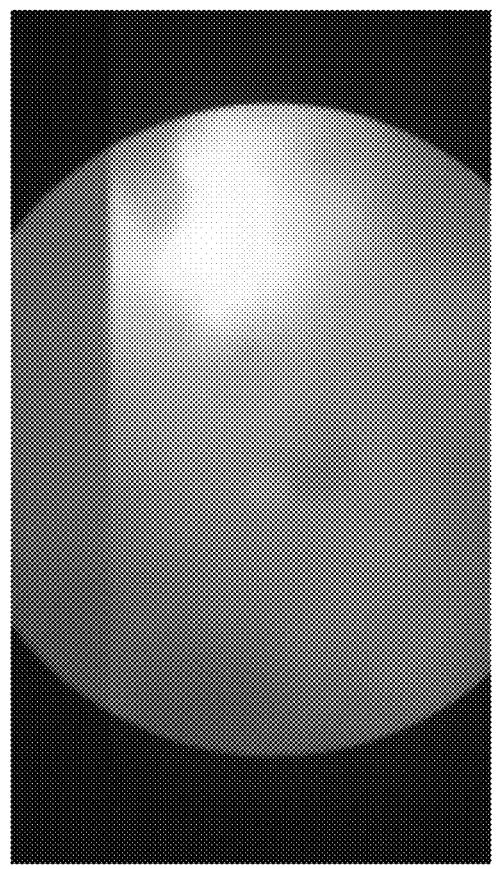
FIG. 4B
LIGHT EVENT 1 AFFECTS TWO FRAMES

500

502
RESETTING A PLURALITY OF ROWS OF PIXELS OF THE ROLLING SHUTTER IMAGER

504
ILLUMINATING THE TISSUE OF THE SUBJECT WITH ILLUMINATION LIGHT FOR AN ILLUMINATION PERIOD

506
SEQUENTIALLY READING CHARGE ACCUMULATED AT THE ROWS OF PIXELS FROM THE FIRST ROW TO THE LAST ROW

508
GENERATING THE FRAME FROM THE READINGS OF CHARGE ACCUMULATED AT THE ROWS OF PIXELS

510
DETERMINING WHETHER THE IMAGE FRAME MEETS ONE OR MORE CRITERIA

512
DETECTING ONE OR MORE ARTIFACTS IN THE FRAME

514
PLACING THE FRAME IN A BUFFER

516
IN ACCORDANCE WITH A DETERMINATION THAT THE IMAGE FRAME DOES NOT MEET THE ONE OR MORE CRITERIA, ADDING THE IMAGE FRAME TO THE VIDEO STREAM

518
IN ACCORDANCE WITH A DETERMINATION THAT THE IMAGE FRAME MEETS THE ONE OR MORE CRITERIA, DISCARDING THE IMAGE FRAME

FIG. 5

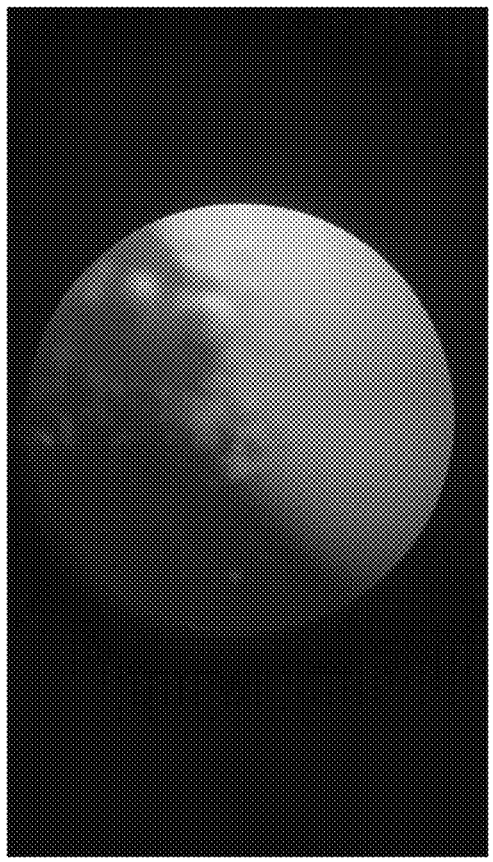
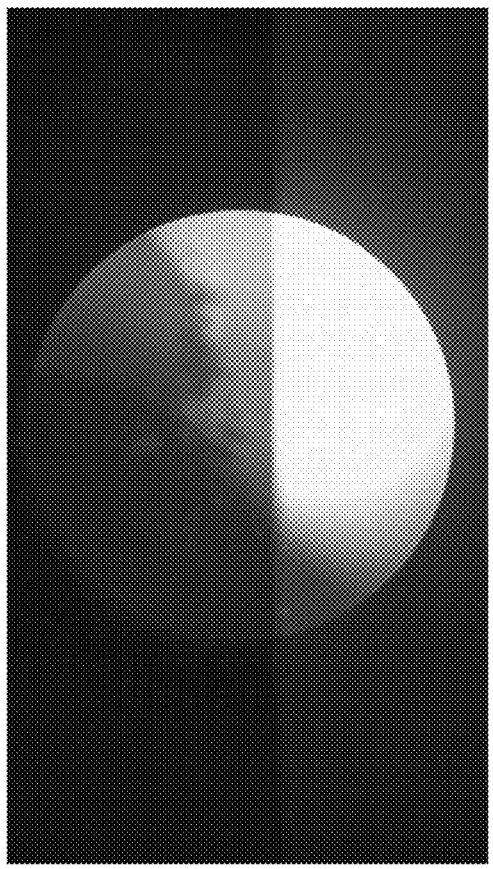
LIGHT EVENT 1 AFFECTS ONE FRAME
FIG. 6B

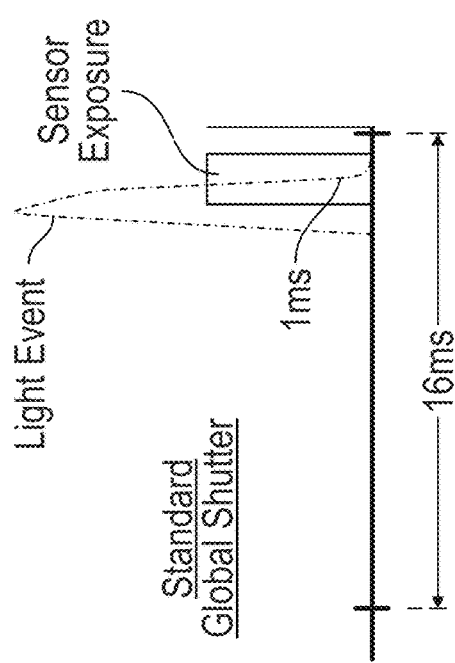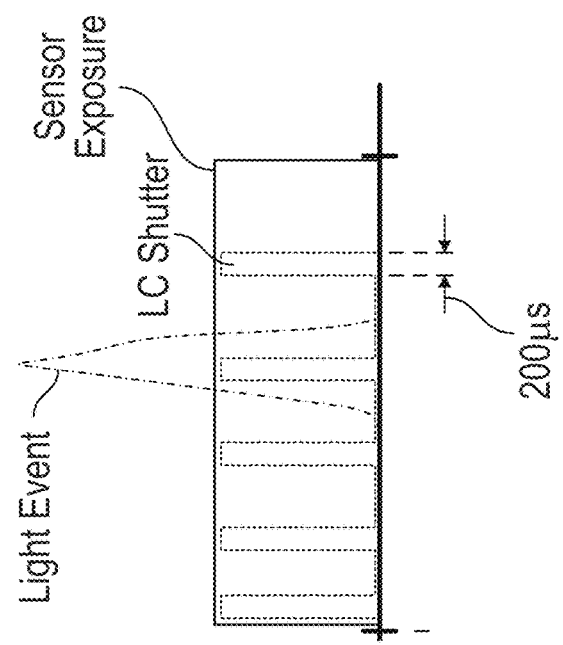

SYSTEMS AND METHODS FOR MITIGATING ARTIFACTS IN MEDICAL IMAGING

CROSS-REFERENCE TO RELATED APPLICATIONS

This application claims the benefit of U.S. Provisional Application No. 63/132,444, filed Dec. 30, 2020, the entire contents of which are hereby incorporated by reference herein.

FIELD

The present disclosure relates generally to medical imaging, and more specifically to techniques for reducing or eliminating artifacts caused by light events in medical imaging.

BACKGROUND

Medical systems, instruments or tools are utilized pre-surgery, during surgery, or post-operatively for various purposes. Some of these medical tools may be used in what are generally termed endoscopic procedures. For example, endoscopy in the medical field allows internal features of the body of a patient to be viewed without the use of traditional, fully invasive surgery. Endoscopic imaging systems incorporate endoscopes to enable a surgeon to view a surgical site, and endoscopic tools enable non-invasive surgery at the site. Endoscopes may be usable along with a camera system for processing the images received by the endoscope. An endoscopic camera system typically includes a camera head connected to a camera control unit (CCU) that processes input image data received from the image sensor of the camera and outputs the image data for display. The CCU may control an illuminator that generates illumination light provided to the imaged scene.

Various imager sensors may be used in endoscopic imaging systems, including charge-coupled device (CCD) sensors and complementary metal oxide semiconductor (CMOS) sensors. The construction of CCDs is generally more complex than the construction of CMOS sensors, and CMOS sensors may be built in high volume wafer fabrication facilities used for related technologies such as microprocessors and chip sets. As a result, CMOS sensors are often less costly than CCDs for similar performance. In addition to lower cost, the common fabrication processes used to create CMOS imagers permits a CMOS pixel array to be integrated on a single circuit with other electronic devices such as clock drivers, digital logic, analog/digital converters, and other suitable electronics. The compact structures possible for a CMOS imager may also reduce space requirements and lower power consumption. CMOS imagers can also have higher sensitivity and provider higher video frame rates.

CMOS based imagers may utilize electronic rolling shutters to expose pixels in the sensor array. With an electronic rolling shutter, rows of pixels are cleared (or reset), exposed, and read out in sequence. During integration, a row of pixels is exposed to light energy and each pixel builds an electric charge corresponding to the amount and wavelengths of light impinging on the pixel. Because the rows are activated and read out in sequence, there is an elapsed time between when the first row integrates and when the last row integrates. Because of the elapsed time between when the first row begins to integrate and when the subsequent rows begin to integrate, a CMOS imager with an electronic rolling shutter may capture video images with blur or other rolling shutter effects. CMOS based imagers may also utilize global shutters to expose pixels in the sensor array. With a global shutter, all rows of pixels are exposed at the same time (i.e., same start and end of exposure) but the readout may be (and usually is) sequential.

During imaging, unintended and/or undesirable light events may occur and cause artifacts in the images. For example, a holmium laser, a laser surgical tool that can be used to remove stones in urology procedures, can produce short-duration and intense light emissions (e.g., in visible or IR wavelengths) when it interacts with the tissue. The light events can generate artifacts in the resulting endoscopic images, such as FIG. 4B as described herein. Other tissue ablation devices such as green light lasers and RF probes may cause similar artifacts. The duration, repetition rate, and amplitude of the light event can be dependent on the energy device.

The unintended/undesirable light events may affect imaging of both sensors having global shutters (e.g., CCD sensors) and sensors having rolling shutters (e.g., CMOS sensors), but can be more pronounced with rolling shutters as described herein. Further, the unintended/undesirable light events may affect various types of frames, including white light frames and fluorescence image frames.

SUMMARY

Described herein are exemplary devices, apparatuses, systems, methods, and non-transitory storage media for medical imaging. More in general are described exemplary devices, systems, and methods for reducing or eliminating artifacts caused by unintended/undesirable light events. The systems, devices, and methods may be used for imaging tissue of a subject, such as in endoscopic imaging procedures. Imaging may be performed pre-operatively, intra-operatively, post-operatively, and during diagnostic imaging sessions and procedures. The imaging methods per se may exclude insertion of an endoscopic imager into a lumen in the body. The endoscopic imager may be inserted into the lumen prior to the imaging methods. The imaging methods per se may exclude any invasive surgical step.

While some of the techniques are described with respect to a certain type of imager (e.g., a rolling shutter imager, a global shutter imager), it should be appreciated that the techniques can be applied in any type of imager. Further, the techniques can be applied in non-surgical or non-medical uses.

An exemplary system may have a "synchronous frame reset" functionality. In a rolling shutter imager, all rows of pixels in the imager sensor can be reset simultaneously or within a short time period (e.g., shorter than a line-by-line offset period of the rolling shutter) using the synchronous frame reset functionality. The rows of pixels can be then illuminated for an illumination period that is less than the time between the synchronous frame reset and the reading of the first row to accumulate charge at the rows of pixels simultaneously for the same amount of time, achieving a global shutter effect. The accumulated charge is then sequentially read from a first row to a last row to generate an image frame. The image frame can then be added to a video stream. The synchronous frame reset functionality can significantly reduce the impact of light events because it shortens the period over which light accumulates at the sensor to less than the frame period. An unintended/undesirable light event occurring before the synchronous frame reset will not affect the image frame. In some examples, the synchronous frame reset step would eliminate impactful light events by around 46%.

An exemplary imaging system may comprise various techniques for detecting artifacts in an image frame. These techniques may involve detecting horizontal or vertical lines in an image frame depending on the mounting orientation of the sensor, detecting a rate of increase in mean values in consecutive image frames, detecting an increase of saturated pixels in consecutive image frames, detecting discrepancies among color channels, detecting an increased amount of light in the field stop region, or any combination thereof. In some examples, machine-learning models can be used to detect artifacts in an image frame, including machine-learning models configured to detect the above-mentioned characteristics.

An exemplary system may use an n-sized buffer. A sequence of frames captured by the imaging system can be accumulated in the buffer. Each image accumulated in the buffer can be associated with a respective score. The score is indicative of how likely the image is compromised by a light event. An image frame can be dropped and replaced in the sequence of images based on a comparison of the scores. The replacement image can be another image in the buffer or a repaired version of the dropped image frame. Advantageously, the N-frame buffer can reduce false-positives and maintain a low drop count. In some examples, the image frame can be repaired using one or more machine-learning models. For example, a trained image transformation model can be configured to receive the compromised image frame and generate an output image in which the artifacts are reduced or eliminated. Additionally or alternatively, a trained machine-learning model can be configured to repair the image frame by correcting the artifact region based on information from other image frames in the buffer.

An exemplary system may comprise a shutter (e.g., a liquid crystal or LC shutter, a mechanical shutter, a DLP mirror, an electromechanical shutter). The shutter can be used with a rolling shutter imager to block light (and thus any unintended/undesirable light events) after the illumination period to eliminate the impact of light events that occur during the sequential readout of the rows. A shutter with pulse width control can be used to break the exposure time into multiple, shorter periods of time to reduce impact to the frame by a light event. The shutter can also be operated as a standalone device without communication with the camera and can block light from the imaging path when a light event is detected.

Any of the techniques described herein can be activated, deactivated, or adjusted in terms of its sensitivity/aggressiveness. In some examples, techniques can be activated, or its sensitivity increased, in response to detection of a light event and/or detection of activation of a surgical energy device. The light event can be detected in a number ways as described herein. It will be appreciated that any of the variations, aspects, features and options described in view of the systems apply equally to the methods and vice versa. It will also be clear that any one or more of the above variations, aspects, features and options can be combined.

According to an aspect is provided a method of imaging tissue of a subject using a rolling shutter imager to provide a video stream, the method comprising: resetting a plurality of rows of pixels of the rolling shutter imager within a time period shorter than a line-by-line offset period of the rolling shutter imager; after resetting the plurality of rows of pixels, illuminating the tissue of the subject with an illumination light for an illumination period to accumulate charge at the plurality of rows of pixels; sequentially reading the accumulated charge at the plurality of rows of pixels from a first row to a last row; and generating an image frame from the sequentially read accumulated charge at the plurality of rows of pixels; and adding the image frame to the video stream.

Optionally, resetting the plurality of rows of pixels of the rolling shutter imager comprises triggering a synchronous frame reset functionality of the rolling shutter imager. The synchronous frame reset functionality can comprise a configurable constant parameter indicating a minimum amount of time the plurality of rows of pixels are exposed after triggering, and the illumination period is configured to be shorter than the constant parameter. The constant parameter can be dynamically adjusted for different image frames.

Optionally, the method further comprises: determining whether the image frame meets one or more criteria; in accordance with a determination that the image frame does not meet the one or more criteria, adding the image frame to the video stream; and in accordance with a determination that the image frame meets the one or more criteria, discarding the image frame. Discarding the image frame can comprise: excluding the image frame from the video stream; and adding a replacement image frame to the video stream.

Optionally, the method further comprises: in accordance with a determination that the image frame does not meet the one or more criteria, processing the image frame using a first configuration of an auto gain control (AGC) algorithm; and in accordance with a determination that the image frame meets the one or more criteria, processing the image frame using a second configuration of the AGC algorithm or foregoing processing the image frame using the AGC algorithm. Determining whether the image frame meets one or more criteria can comprise identifying one or more artifacts in the image frame. The one or more artifacts can be identified in real time. Identifying one or more artifacts in the image frame can comprise identifying a line in the image frame.

Optionally, the method further comprises: applying a Sobel filter to the image frame.

Optionally, identifying one or more artifacts in the image frame comprises: calculating a rate of increase from mean values of one or more previous image frames to a mean value of the image frame. The rate of increase can be calculated with respect to a region of interest in the image frame.

Optionally, identifying one or more artifacts in the image frame comprises: calculating an increase from a number of saturated pixels in a previous image frame to a number of saturated pixels in the image frame. The increase can be calculated with respect to a region of interest in the image frame.

Optionally, identifying one or more artifacts in the image frame comprises: evaluating a difference between at least two of a red channel, a blue channel, and a green channel of the image frame.

Optionally, identifying one or more artifacts in the image frame comprises: processing the image frame using a trained machine-learning algorithm. The trained machine-learning algorithm can be a neural network.

Optionally, identifying one or more artifacts in the image frame comprises: detecting an increased amount of light in a field stop region of the image frame.

Optionally, the method further comprises: placing the image frame into a buffer of a predefined size; comparing all frames placed in the buffer; and based on the comparison, excluding one or more frames in the buffer from the video stream. The pre-defined size can be three image frames.

Comparing all frames placed in the buffer can comprise assigning a score to each frame placed in the buffer; and comparing the scores of all frames placed in the buffer.

Optionally, the method further comprises: automatically tuning one or more parameters of the method. The one or more parameters can comprise one or more thresholds for identifying an artifact in the image frame, a size of an image buffer, a maximum number of image frames droppable from the image buffer, a maximum number of consecutive image frames droppable from the image buffer, or any combination thereof.

Optionally, the method further comprises: automatically tuning the one or more parameters in response to detecting a light event or detecting activation of a surgical energy device. Detecting activation of the surgical energy device can comprise receiving a signal from the surgical energy device. The surgical energy device can be a laser unit. The surgical energy device can be an RF probe. Detecting activation of the surgical energy device can comprise detecting an increase in power consumption of the surgical energy device. Detecting the light event can comprise receiving a signal from a photodetector mounted in the rolling shutter imager. Detecting activation of the surgical energy device can comprise receiving acoustic signals from the surgical energy device.

Optionally, the method further comprises: automatically tuning the one or more parameters based on detected motion of the imager.

Optionally, the imager comprises a shutter component, and the shutter is configured to close at the end of the illumination period.

Optionally, the shutter component comprises: a liquid crystal shutter, a mechanical shutter, a DLP mirror, or an electromechanical shutter.

Optionally, the illumination light is generated by at least one LED.

Optionally, the rolling shutter imager is part of an endoscopic imager.

According to an aspect is provided a computer-implemented method of providing a video stream comprising: accumulating a sequence of images in a buffer of a pre-defined size, wherein each image of the sequence is associated with a respective score; comparing the scores of the sequence of images in the buffer; based on the comparison, identifying an image of the sequence of images; removing the identified image from the sequence of images to obtain an updated sequence; and adding the updated sequence of images to the video stream.

Optionally, the sequence of images are obtained by a rolling shutter imager.

Optionally, the sequence of images are obtained by a global shutter imager configured to read multiple rows of pixels simultaneously.

Optionally, the sequence of images are obtained by an endoscopic imager.

Optionally, the method further comprises: replacing the identified image with a replacement image in the sequence of images.

Optionally, the method further comprises: for each image in the sequence of images: identifying one or more artifacts in the respective image; and assigning the respective score to the image based on the identification. Identifying one or more artifacts in the image can comprise identifying a line in the image. Identifying one or more artifacts in the image can comprise calculating a rate of increase from mean values of one or more previous images to a mean value of the image. The rate of increase can be calculated with respect to a region of interest in the image frame.

Optionally, identifying one or more artifacts in the image comprises: calculating an increase from a number of saturated pixels in a previous image to a number of saturated pixels in the image. The increase can be calculated with respect to a region of interest in the image frame.

Optionally, identifying one or more artifacts in the image comprises: evaluating a difference between at least two of a red channel, a blue channel, and a green channel of the image.

Optionally, identifying one or more artifacts in the image comprises: processing the image using a trained machine-learning algorithm. The trained machine-learning algorithm can be a neural network Optionally, identifying one or more artifacts in the image frame comprises: detecting an increased amount of light in a field stop of the image frame.

Optionally, the method further comprises: automatically adjusting the pre-defined size of the buffer.

Optionally, the method further comprises: automatically increasing the pre-defined size of the buffer in response to detecting a light event or detecting activation of a surgical energy device.

According to an aspect is provided a method of generating an image using an endoscopic imager comprises: in a frame period: accumulating charge at an array of pixels of the endoscopic imager during the frame period; deactivating, for n times, a shutter component for one n-th or less of a pre-defined exposure period to permit light through the shutter; and after deactivating the shutter component for the n-th time, generating the image from readings of charge accumulated at the arrays of pixels. The method may exclude insertion of the endoscopic imager into a lumen in the body. The endoscopic imager may be inserted into the lumen prior to the method.

Optionally, the shutter component comprises: a liquid crystal shutter, a mechanical shutter, a DLP mirror, or an electromechanical shutter.

Optionally, the endoscopic imager is a rolling shutter imager.

Optionally, the endoscopic imager is a global shutter imager.

Optionally, the deactivations of the shutter are spaced apart by at least the pre-defined exposure period.

Optionally, the method further comprises: automatically adjusting the value of n. The value of n can be equal to or larger than 1.

According to an aspect is provided a method of shielding an endoscopic imager from a light event comprising: detecting the light event; and responsive to detecting the light event, activating a shutter to shield a sensor of the endoscopic imager from the light event.

Optionally, the shutter comprises: a liquid crystal shutter, a mechanical shutter, a DLP mirror, or an electromechanical shutter.

Optionally, detecting the light event comprises detecting the light event via a photodiode detector.

Optionally, the light event comprises infrared light.

Optionally, the light event is generated by a laser. The laser can be a holmium laser.

Optionally, the method further comprises: automatically deactivating the shutter after a pre-defined period of time. The pre-defined period of time can be approximately between 500 us to 1 ms. The pre-defined period of time can be dynamically adjustable.

Optionally, the method further comprises: automatically deactivating the shutter component responsive to detecting an absence of the light event.

Optionally, the endoscopic imager is a rolling shutter imager.

Optionally, the endoscopic imager is a global shutter imager.

According to an aspect is provided a system for imaging tissue of a subject to provide a video stream comprises: an illumination source; and an imaging apparatus that comprises an electronic rolling shutter imager, the imaging apparatus being configured for: resetting a plurality of rows of pixels of the rolling shutter imager within a time period shorter than a line-by-line offset period of the rolling shutter imager; after resetting the plurality of rows of pixels, illuminating the tissue of the subject with an illumination light for an illumination period to accumulate charge at the plurality of rows of pixels; sequentially reading the accumulated charge at the plurality of rows of pixels from a first row to a last row; and generating an image frame from the sequentially read accumulated charge at the plurality of rows of pixels; and adding the image frame to the video stream.

Optionally, resetting the plurality of rows of pixels of the rolling shutter imager comprises triggering a synchronous frame reset functionality of the rolling shutter imager. The synchronous frame reset functionality can comprise a configurable constant parameter indicating a minimum amount of time the plurality of rows of pixels are exposed after triggering, and the illumination period is configured to be shorter than the constant parameter. The constant parameter can be dynamically adjusted for different image frames.

Optionally, the imaging apparatus is configured for: determining whether the image frame meets one or more criteria; in accordance with a determination that the image frame does not meet the one or more criteria, adding the image frame to the video stream; and in accordance with a determination that the image frame meets the one or more criteria, discarding the image frame. Discarding the image frame can comprise excluding the image frame from the video stream; and adding a replacement image frame to the video stream.

Optionally, the imaging apparatus is further configured for: in accordance with a determination that the image frame does not meet the one or more criteria, processing the image frame using a first configuration of an auto gain control (AGC) algorithm; and in accordance with a determination that the image frame meets the one or more criteria, processing the image frame using a second configuration of the AGC algorithm or foregoing processing the image frame using the AGC algorithm. Determining whether the image frame meets one or more criteria can comprise identifying one or more artifacts in the image frame. The one or more artifacts can be identified in real time.

Optionally, identifying one or more artifacts in the image frame comprises: identifying a line in the image frame.

Optionally, the imaging apparatus further is configured for applying a Sobel filter to the image frame.

Optionally, identifying one or more artifacts in the image frame comprises: calculating a rate of increase from mean values of one or more previous image frames to a mean value of the image frame. The rate of increase can be calculated with respect to a region of interest in the image frame.

Optionally, identifying one or more artifacts in the image frame comprises: calculating an increase from a number of saturated pixels in a previous image frame to a number of saturated pixels in the image frame. The increase can be calculated with respect to a region of interest in the image frame.

Optionally, identifying one or more artifacts in the image frame comprises: evaluating a difference between at least two of a red channel, a blue channel, and a green channel of the image frame.

Optionally, identifying one or more artifacts in the image frame comprises: processing the image frame using a trained machine-learning algorithm. The trained machine-learning algorithm can be a neural network.

Optionally, identifying one or more artifacts in the image frame comprises: detecting an increased amount of light in a field stop region of the image frame.

Optionally, the imaging apparatus further is configured for: placing the image frame into a buffer of a predefined size; comparing all frames placed in the buffer; and based on the comparison, excluding one or more frames in the buffer from the video stream. The pre-defined size can be three image frames. Comparing all frames placed in the buffer can comprise assigning a score to each frame placed in the buffer; and comparing the scores of all frames placed in the buffer.

Optionally, the imaging apparatus further is configured for: automatically tuning one or more parameters of the method. The one or more parameters can comprise: one or more thresholds for identifying an artifact in the image frame, a size of an image buffer, a maximum number of image frames droppable from the image buffer, a maximum number of consecutive image frames droppable from the image buffer, or any combination thereof.

Optionally, the imaging apparatus further is configured for: automatically tuning the one or more parameters in response to detecting a light event or detecting activation of a surgical energy device. Detecting activation of the surgical energy device can comprise receiving a signal from the surgical energy device. The surgical energy device can be a laser unit. The surgical energy device can be an RF probe. Detecting activation of the surgical energy device can comprise detecting an increase in power consumption of the surgical energy device. Detecting the light event can comprise receiving a signal from a photodetector mounted in the rolling shutter imager. Detecting activation of the surgical energy device can comprise receiving acoustic signals from the surgical energy device.

Optionally, the imaging apparatus further is configured for automatically tuning the one or more parameters based on detected motion of the imager.

Optionally, the imager comprises a shutter component, and the shutter is configured to close at the end of the illumination period. The shutter component can comprise a liquid crystal shutter, a mechanical shutter, a DLP mirror, or an electromechanical shutter.

Optionally, the illumination light is generated by at least one LED.

Optionally, the rolling shutter imager is part of an endoscopic imager.

According to an aspect is provided a system for providing a video stream comprising: one or more processors; a memory; and one or more programs, wherein the one or more programs are stored in the memory and configured to be executed by the one or more processors, the one or more programs including instructions for: accumulating a sequence of images in a buffer of a pre-defined size, wherein each image of the sequence is associated with a respective score; comparing the scores of the sequence of images in the buffer; based on the comparison, identifying an image of the sequence of images; removing the identified image from the sequence of images to obtain an updated sequence; and adding the updated sequence of images to the video stream.

Optionally, the sequence of images are obtained by a rolling shutter imager.

Optionally, the sequence of images are obtained by a global shutter imager configured to read multiple rows of pixels simultaneously.

Optionally, the sequence of images are obtained by an endoscopic imager.

Optionally, the one or more programs further include instructions for: replacing the identified image with a replacement image in the sequence of images.

Optionally, the one or more programs further include instructions for: for each image in the sequence of images: identifying one or more artifacts in the respective image; and assigning the respective score to the image based on the identification.

Optionally, identifying one or more artifacts in the image comprises: identifying a line in the image.

Optionally, identifying one or more artifacts in the image comprises: calculating a rate of increase from mean values of one or more previous images to a mean value of the image. The rate of increase can be calculated with respect to a region of interest in the image frame.

Optionally, identifying one or more artifacts in the image comprises: calculating an increase from a number of saturated pixels in a previous image to a number of saturated pixels in the image. The increase can be calculated with respect to a region of interest in the image frame.

Optionally, identifying one or more artifacts in the image comprises: evaluating a difference between at least two of a red channel, a blue channel, and a green channel of the image.

Optionally, identifying one or more artifacts in the image comprises: processing the image using a trained machine-learning algorithm. The trained machine-learning algorithm can be a neural network.

Optionally, identifying one or more artifacts in the image frame comprises: detecting an increased amount of light in a field stop of the image frame.

Optionally, the one or more programs further include instructions for: automatically adjusting the pre-defined size of the buffer.

Optionally, the one or more programs further include instructions for: automatically increasing the pre-defined size of the buffer in response to detecting a light event or detecting activation of a surgical energy device.

According to an aspect is provided a system for generating an image using an endoscopic imager comprises: a shutter component and an imaging apparatus being configured for: in a frame period: accumulating charge at an array of pixels of the endoscopic imager during the frame period; deactivating, for n times, the shutter component for one n-th or less of a pre-defined exposure period to permit light through the shutter; and after deactivating the shutter component for the n-th time, generating the image from readings of charge accumulated at the arrays of pixels.

Optionally, the shutter component comprises: a liquid crystal shutter, a mechanical shutter, a DLP mirror, or an electromechanical shutter.

Optionally, the endoscopic imager is a rolling shutter imager.

Optionally, the endoscopic imager is a global shutter imager.

Optionally, the deactivations of the shutter are spaced apart by at least the pre-defined exposure period.

Optionally, the imaging apparatus is configured for: automatically adjusting the value of n. The value of n can be equal to or larger than 1.

According to an aspect is provided a system for shielding an endoscopic imager from a light event comprising: a shutter and an imaging apparatus being configured for: detecting the light event; and responsive to detecting the light event, activating a shutter to shield a sensor of the endoscopic imager from the light event.

Optionally, the shutter comprises: a liquid crystal shutter, a mechanical shutter, a DLP mirror, or an electromechanical shutter.

Optionally, detecting the light event comprises detecting the light event via a photodiode detector.

Optionally, the light event comprises infrared light.

Optionally, the light event is generated by a laser. The laser can be a holmium laser.

Optionally, the imaging apparatus is configured for: automatically deactivating the shutter after a pre-defined period of time. The pre-defined period of time can be approximately between 500 us to 1 ms. The pre-defined period of time can be dynamically adjustable.

Optionally, the imaging apparatus is configured for: automatically deactivating the shutter component responsive to detecting an absence of the light event.

Optionally, the endoscopic imager is a rolling shutter imager.

Optionally, the endoscopic imager is a global shutter imager.

According to an aspect is provided a method of imaging tissue of a subject using a rolling shutter imager to provide a video stream comprises: sequentially resetting a plurality of rows of pixels of the rolling shutter imager from a first row to a last row; transitioning a liquid crystal shutter from a closed state to an open state; after the liquid crystal shutter is transitioned into the open state and after resetting the last row, illuminating the tissue of the subject with an illumination light for an illumination period to accumulate charge at the plurality of rows of pixels, and after the illumination period ends, sequentially reading the accumulated charge at the rows of pixels from the first row to the last row; generating an image frame from the sequentially read accumulated charge at the plurality of rows of pixels; and adding the image frame to the video stream.

Optionally, the illumination period is at least a portion of the time period between when the last row is reset and when the first row is read.

Optionally, the illumination period starts when the last row is reset.

Optionally, the plurality of rows of pixels is exposed for the same period of time to generate the image.

Optionally, the method further comprises: after the end of the illumination period, starting transitioning the liquid crystal shutter from the open state to the closed state.

Optionally, the method further comprises: at the end of the illumination period, starting transitioning the liquid crystal shutter from the open state to the closed state.

Optionally, the method further comprises: before the end of the illumination period, starting transitioning the liquid crystal shutter from the open state to the closed state.

Optionally, the liquid crystal shutter is opened or closed using a timer device based on a vertical sync pulse.

Optionally, the liquid crystal shutter is opened or closed based on one or more characteristics of an imaged scene. The one or more characteristics of the imaged scene can comprise brightness and/or modality of the imaged scene.

Optionally, the illumination light is generated by at least one LED.

Optionally, the rolling shutter imager is part of an endoscopic imager.

Optionally, the rolling shutter imager is part of a flexible and/or chip-on-tip scope.

According to an aspect is provided a system for imaging tissue of a subject to provide a video stream comprising: an illumination source; and an imaging apparatus that comprises a rolling shutter imager, the imaging apparatus being configured for: sequentially resetting a plurality of rows of pixels of the rolling shutter imager from a first row to a last row; transitioning a liquid crystal shutter from a closed state to an open state; after the liquid crystal shutter is transitioned into the open state and after resetting the last row, illuminating the tissue of the subject with the illumination source for an illumination period to accumulate charge at the plurality of rows of pixels, and after the illumination period ends, sequentially reading the accumulated charge at the rows of pixels from the first row to the last row; generating an image frame from the sequentially read accumulated charge at the plurality of rows of pixels; and adding the image frame to the video stream.

Optionally, the illumination period is at least a portion of the time period between when the last row is reset and when the first row is read.

Optionally, the illumination period starts when the last row is reset.

Optionally, the plurality of rows of pixels is exposed for the same period of time to generate the image.

Optionally, the imaging apparatus is further configured for: after the end of the illumination period, starting transitioning the liquid crystal shutter from the open state to the closed state.

Optionally, the imaging apparatus is further configured for: at the end of the illumination period, starting transitioning the liquid crystal shutter from the open state to the closed state.

Optionally, the imaging apparatus is further configured for: before the end of the illumination period, starting transitioning the liquid crystal shutter from the open state to the closed state.

Optionally, the liquid crystal shutter is opened or closed using a timer device based on a vertical sync pulse.

Optionally, the liquid crystal shutter is opened or closed based on one or more characteristics of an imaged scene. The one or more characteristics of the imaged scene can comprise brightness and/or modality of the imaged scene.

Optionally, the illumination source comprises at least one LED.

Optionally, the rolling shutter imager is part of an endoscopic imager.

Optionally, the rolling shutter imager is part of a flexible and/or chip-on-tip scope.

BRIEF DESCRIPTION OF THE FIGURES

The invention will now be described, by way of example only, with reference to the accompanying drawings, in which:

FIG. 4B illustrates exemplary artifacts in two image frames, according to some examples;

FIG. 5 provides an exemplary method for imaging tissue of a subject using a rolling shutter imager to provide a video stream, according to some examples;

FIG. 6B illustrates exemplary artifacts in an image frame, according to some examples;

FIG. 8A illustrates how a light event can impact an exposure period, according to some examples;

FIG. 8B illustrates using a shutter to mitigate impact of a light event to an image frame, according to some examples;

DETAILED DESCRIPTION

Figure 1:
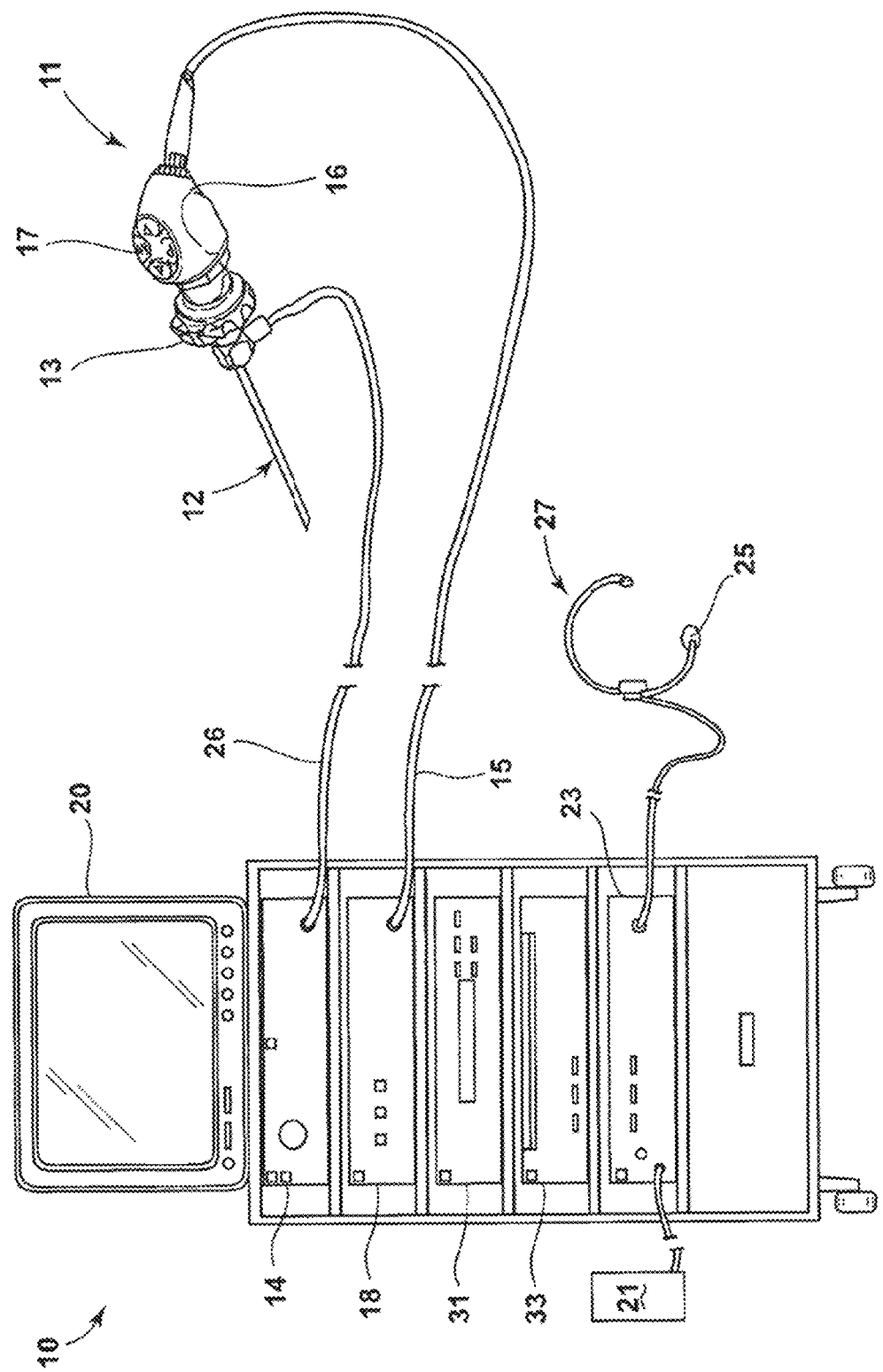
FIG. 1 is an illustration of an endoscopic camera system, according to some examples.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described. Examples will now be described more fully hereinafter with reference to the accompanying drawings; however, they may be embodied in different forms and should not be construed as limited to the examples set forth herein. Rather, these examples are provided so that this disclosure will be thorough and complete, and will fully convey exemplary implementations to those skilled in the art.

Described herein are exemplary devices, apparatuses, systems, methods, and non-transitory storage media for medical imaging. More in general are described exemplary devices, systems, and methods for reducing or eliminating artifacts caused by unintended/undesirable light events. The systems, devices, and methods may be used for imaging tissue of a subject, such as in endoscopic imaging procedures. Imaging may be performed pre-operatively, intra-operatively, post-operatively, and during diagnostic imaging sessions and procedures. The imaging methods per se may exclude insertion of an endoscopic imager into a lumen in the body. The endoscopic imager may be inserted into the lumen prior to the imaging methods. The imaging methods per se may exclude any invasive surgical step.

While some of the techniques are described with respect to a certain type of imager (e.g., a rolling shutter imager, a global shutter imager), it should be appreciated that the techniques can be applied in any type of imager. Further, the techniques can be applied in non-surgical or non-medical uses.

An exemplary system may have a "synchronous frame reset" functionality. In a rolling shutter imager with this functionality, all rows of pixels in the imager sensor can be reset simultaneously or within a short time period (e.g., shorter than a line-by-line offset period of the rolling shutter) using the synchronous frame reset functionality. The rows of pixels are then illuminated for an illumination period that is less than the time between the synchronous frame reset and the reading of the first row to accumulate charge at the rows of pixels simultaneously for the same amount of time, achieving a global shutter effect. The accumulated charge is then sequentially read from a first row to a last row to generate an image frame. The image frame can then be added to a video stream. The synchronous frame reset functionality can significantly reduce the impact of light events because it shortens the period over which light accumulates at the sensor to less than the frame period. An unintended/undesirable light event occurring before the synchronous frame reset will not affect the image frame. In some examples, the synchronous frame reset step would eliminate impactful light events by around 46%.

An exemplary imaging system may comprise various techniques for detecting artifacts in an image frame. These techniques may involve detecting horizontal lines in an image frame, detecting a rate of increase in mean values in consecutive image frames, detecting an increase of saturated pixels in consecutive image frames, detecting discrepancies among color channels, using machine-learning models, detecting an increased amount of light in the field stop region, or any combination thereof. In some examples, machine-learning models can be used to detect artifacts in an image frame, including machine-learning models configured to detect the above-mentioned characteristics.

An exemplary system may use an n-sized buffer. A sequence of frames captured by the imaging system can be accumulated in the buffer. Each image accumulated in the buffer can be associated with a respective score. The score is indicative of how likely the image is compromised by a light event. An image frame can be dropped and replaced in the sequence of images based on a comparison of the scores. Advantageously, the N-frame buffer can reduce false-positives and maintain a low drop count.

An exemplary system may comprise a shutter (e.g., a liquid crystal shutter, a mechanical shutter, a DLP mirror, an electromechanical shutter). The shutter can be used with a rolling shutter imager to block light (and thus any unintended or undesirable light events) after the illumination period to eliminate the impact of light events that occur during the sequential readout of the rows. A shutter with pulse width control can be used to break the exposure time into multiple, shorter periods of time to reduce impact to the frame by a light event. The shutter can also be operated as a standalone device without communication with the camera and can block light from the imaging path when a light event is detected.

Any of the techniques described herein can be activated, deactivated, or adjusted in terms of its sensitivity/aggressiveness. In some examples, a technique can be activated, or its sensitivity increased, in response to detection of a light event and/or detection of activation of a surgical energy device. The detection can be performed in a number ways as described herein.

In various examples, such as those described above, the illumination light may be modulated using pulse width modulation to provide the right amount of illumination to the scene. The imaging system may control the amount of light so that the imaging sensor or sensors are optimally exposed and may do so based on intensity at the sensor(s) during one or more previous frames.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 shows an example of an endoscopic imaging system 10, which includes a scope assembly 11 which may be utilized in endoscopic procedures. The scope assembly 11 incorporates an endoscope or scope 12 which is coupled to a camera head 16 by a coupler 13 located at the distal end of the camera head 16. Light is provided to the scope by a light source 14 via a light guide 26, such as a fiber optic cable. The camera head 16 is coupled to a camera control unit (CCU) 18 by an electrical cable 15. The CCU 18 is connected to, and communicates with, the light source 14. Operation of the camera 16 is controlled, in part, by the CCU 18. The cable 15 conveys video image and/or still image data from the camera head 16 to the CCU 18 and may convey various control signals bi-directionally between the camera head 16 and the CCU 18.

A control or switch arrangement 17 may be provided on the camera head 16 for allowing a user to manually control various functions of the system 10, which may include switch from one imaging mode to another, as discussed further below. Voice commands may be input into a microphone 25 mounted on a headset 27 worn by the practitioner and coupled to the voice-control unit 23. A hand-held control device 29, such as a tablet with a touch screen user interface or a PDA, may be coupled to the voice control unit 23 as a further control interface. In the illustrated example, a recorder 31 and a printer 33 are also coupled to the CCU 18. Additional devices, such as an image capture and archiving device, may be included in the system 10 and coupled to the CCU 18. Video image data acquired by the camera head 16 and processed by the CCU 18 is converted to images, which can be displayed on a monitor 20, recorded by recorder 31, and/or used to generate static images, hard copies of which can be produced by the printer 33.

Figure 2:
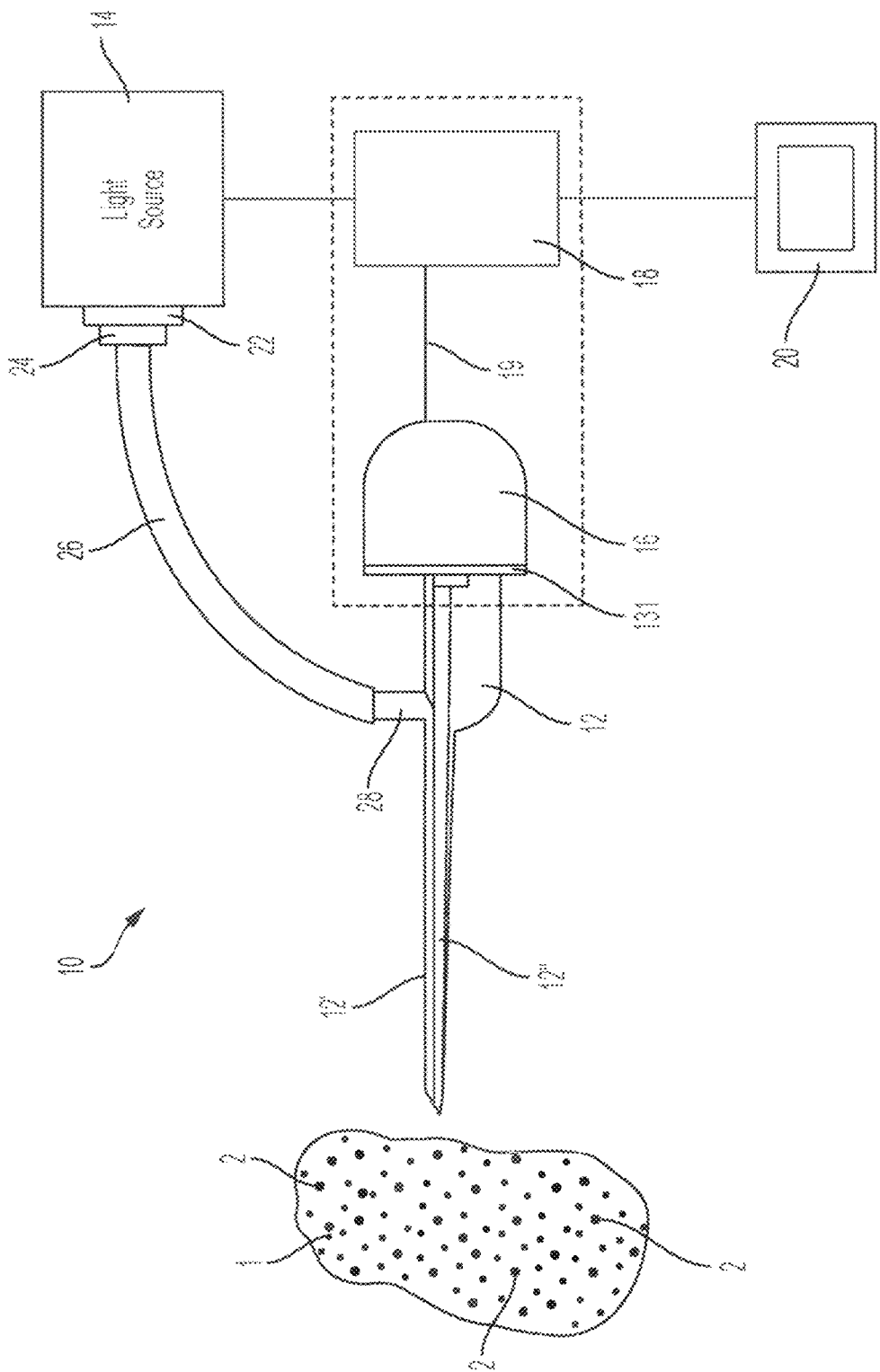
FIG. 2 is a diagram of a portion of the endoscopic camera system of FIG. 1 and a target object for imaging, according to some examples.

FIG. 2 shows an example of a portion of the endoscopic system 10 being used to illuminate and receive light from an object 1, such as a surgical site of a patient. The object 1 may include includes fluorescent markers 2, for example, as a result of the patient being administered a fluorescence imaging agent. The fluorescent markers 2 may be comprised of, for example, indocyanine green (ICG).

The light source 14 can generate visible illumination light (such as any combination of red, green, and blue light) for generating visible (e.g., white light) images of the target object 1 and can also produce fluorescence excitation illumination light for exciting the fluorescent markers 2 in the target object for generating fluorescence images. Illumination light is transmitted to and through an optic lens system 22 which focuses light onto a light pipe 24. The light pipe 24 may create a homogeneous light, which is then transmitted to the fiber optic light guide 26. The light guide 26 may include multiple optic fibers and is connected to a light post 28, which is part of the endoscope 12. The endoscope 12 includes an illumination pathway 12' and an optical channel pathway 12".

The endoscope 12 may include a notch filter 131 that allows some or all (preferably, at least 80%) of fluorescence emission light (e.g., in a wavelength range of 830 nm to 870 nm) emitted by fluorescence markers 2 in the target object 1 to pass therethrough and that allows some or all (preferably, at least 80%) of visible light (e.g., in the wavelength range of 400 nm to 700 nm), such as visible illumination light reflected by the target object 1, to pass therethrough, but that blocks substantially all of the fluorescence excitation light (e.g., infrared light having a wavelength of 808 nm) that is used to excite fluorescence emission from the fluorescent marker 2 in the target object 1. The notch filter 131 may have an optical density of OD5 or higher. In some examples, the notch filter 131 can be located in the coupler 13.

Figure 3:
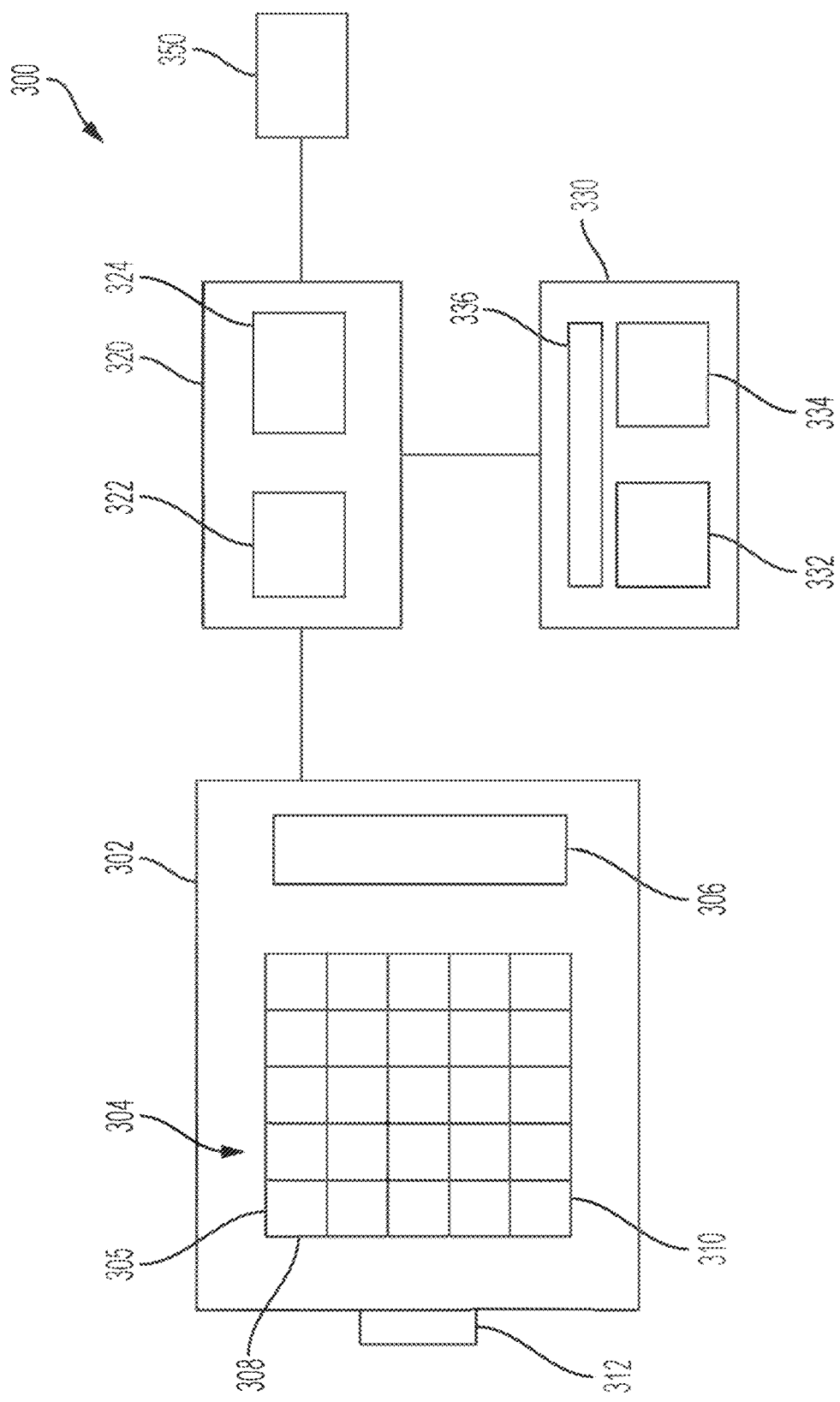
FIG. 3 is a block diagram of an imaging system, according to some examples.

FIG. 3 schematically illustrates an exemplary imaging system 300 that employs an electronic imager 302 to generate images (e.g., still and/or video) of a target object, such as a target tissue of a patient, according to some examples.

The imager 302 may be a rolling shutter imager (e.g., CMOS sensors) or a global shutter imager (e.g., CCD sensors). System 300 may be used, for example, for the endoscopic imaging system 10 of FIG. 1. The imager 302 includes a CMOS sensor 304 having an array of pixels 305 arranged in rows of pixels 308 and columns of pixels 310. The imager 302 may include control components 306 that control the signals generated by the CMOS sensor 304. Examples of control components include gain circuitry for generating a multi-bit signal indicative of light incident on each pixel of the sensor 304, one or more analog-to-digital converters, one or more line drivers to act as a buffer and provide driving power for the sensor 304, row circuitry, and timing circuitry. A timing circuit may include components such as a bias circuit, a clock/timing generation circuit, and/or an oscillator. Row circuitry may enable one or more processing and/or operational tasks such as addressing rows of pixels 308, addressing columns of pixels 310, resetting charge on rows of pixels 308, enabling exposure of pixels 305, decoding signals, amplifying signals, analog-to-digital signal conversion, applying timing, read out and reset signals and other suitable processes or tasks. Imager 302 may also include a mechanical shutter 312 that may be used, for example, to control exposure of the image sensor 304 and/or to control an amount of light received at the image sensor 304.

One or more control components may be integrated into the same integrated circuit in which the sensor 304 is integrated or may be discrete components. The imager 302 may be incorporated into an imaging head, such as camera head 16 of system 10.

One or more control components 306, such as row circuitry and a timing circuit, may be electrically connected to an imaging controller 320, such as camera control unit 18 of system 10. The imaging controller 320 may include one or more processors 322 and memory 324. The imaging controller 320 receives imager row readouts and may control readout timings and other imager operations, including mechanical shutter operation. The imaging controller 320 may generate image frames, such as video frames from the row and/or column readouts from the imager 302. Generated frames may be provided to a display 350 for display to a user, such as a surgeon.

The system 300 in this example includes a light source 330 for illuminating a target scene. The light source 330 is controlled by the imaging controller 320. The imaging controller 320 may determine the type of illumination provided by the light source 330 (e.g., white light, fluorescence excitation light, or both), the intensity of the illumination provided by the light source 330, and or the on/off times of illumination in synchronization with rolling shutter operation. The light source 330 may include a first light generator 332 for generating light in a first wavelength and a second light generator 334 for generating light in a second wavelength. For example, in some examples, the first light generator 332 is a white light generator, which may be comprised of multiple discrete light generation components (e.g., multiple LEDs of different colors), and the second light generator 334 is a fluorescence excitation light generator, such as a laser diode.

The light source 330 includes a controller 336 for controlling light output of the light generators. The controller 336 may be configured to provide pulse width modulation of the light generators for modulating intensity of light provided by the light source 330, which can be used to manage over-exposure and under-exposure. In some examples, nominal current and/or voltage of each light generator remains constant and the light intensity is modulated by switching the light generators (e.g., LEDs) on and off according to a pulse width control signal. In some examples, a PWM control signal is provided by the imaging controller 336. This control signal can be a waveform that corresponds to the desired pulse width modulated operation of light generators.

The imaging controller 320 may be configured to determine the illumination intensity required of the light source 330 and may generate a PWM signal that is communicated to the light source 330. In some examples, depending on the amount of light received at the sensor 304 and the integration times, the light source may be pulsed at different rates to alter the intensity of illumination light at the target scene. The imaging controller 320 may determine a required illumination light intensity for a subsequent frame based on an amount of light received at the sensor 304 in a current frame and/or one or more previous frames. In some examples, the imaging controller 320 is capable of controlling pixel intensities via PWM of the light source 330 (to increase/decrease the amount of light at the pixels), via operation of the mechanical shutter 312 (to increase/decrease the amount of light at the pixels), and/or via changes in gain (to increase/decrease sensitivity of the pixels to received light). In some examples, the imaging controller 320 primarily uses PWM of the illumination source for controlling pixel intensities while holding the shutter open (or at least not operating the shutter) and maintaining gain levels. The controller 320 may operate the shutter 312 and/or modify the gain in the event that the light intensity is at a maximum or minimum and further adjustment is needed.

Undesirable Light Events Affecting Global and Rolling Shutters

During imaging, unintended and/or undesirable light events may occur and cause artifacts in the images. For example, a holmium laser, a laser surgical tool that can be used to remove stones in urology procedures, can produce short-duration and intense light emissions (e.g., in visible or IR wavelengths) when it interacts with the tissue. The light events can generate artifacts in the resulting endoscopic images, such as FIG. 4B as described herein. Other tissue ablation devices such as green light lasers and RF probes may cause similar artifacts. The duration, repetition rate, and amplitude of the light event can be dependent on the energy device.

While unintended/undesirable light events may affect imaging by both sensors having global shutters (e.g., CCD sensors) and rolling shutters (e.g., CMOS sensors), the artifacts can be more pronounced with rolling shutters. With a global shutter image sensor, all pixels of the sensor array are exposed simultaneously, and the sensor array is only sensitive to light during the exposure window. Thus, an unintended/undesirable light event would only generate artifacts if the light event lines up with the exposure window. For example, at a frame rate of 60 Hertz, a frame is captured in a 16.6-millisecond cycle. If the sensor array is exposed for only 1 millisecond of the 16.6-millisecond cycle, an unintended/undesirable light event would only generate artifacts in the frame if the light event happens to occur during the 1-millisecond exposure window. For this reason, artifacts may occur less frequently with a global shutter image sensor than with a rolling shutter image sensor.

Further, a global shutter image sensor may provide interlaced scanning, which can further alleviate artifacts caused by unintended/undesirable light events. During an interlaced scan, one-half of the horizontal pixel rows (e.g., the even-numbered rows) are captured in one cycle and the other half (e.g., the odd-numbered rows) in the next, so two complete scans are required to capture a frame. Thus, if the unintended/undesirable light event occurred during one cycle, it would only affect half of the frame. For this additional reason, artifacts may be less pronounced with a global shutter image sensor.

Figure 4A:
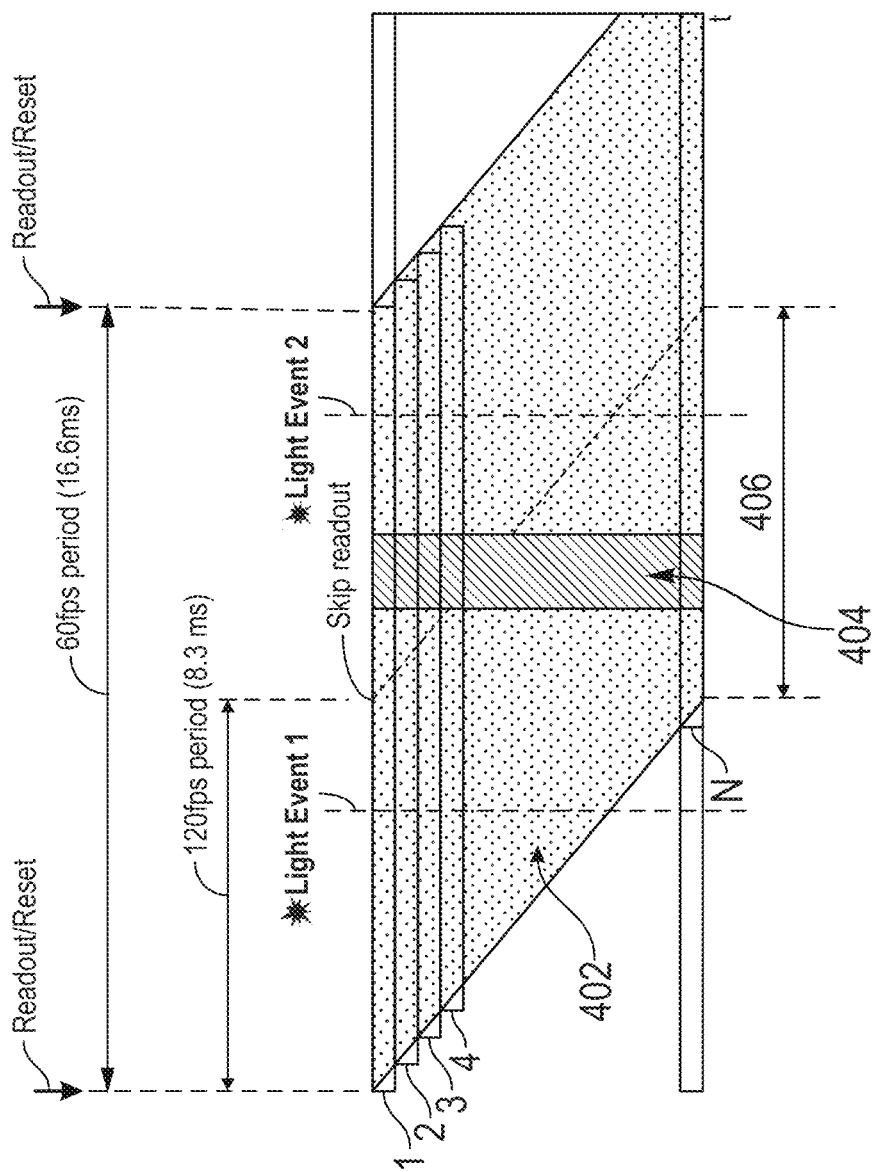
FIG. 4A is a diagram showing how unintended/undesirable light events can generate artifacts with a rolling shutter image sensor having a "global shutter" period, according to some examples.

With a rolling shutter image sensor, however, artifacts can be more frequent and more pronounced. FIG. 4A depicts how unintended/undesirable light events can generate artifacts with an exemplary rolling shutter image sensor having a "global shutter" period. In the depicted system, illumination to a target scene (e.g., target tissue of a patient) is controlled to produce a global shutter-type effect with a long integration time for the imaging sensor(s) pixels, as described below. While FIG. 4A illustrates how unintended/undesirable light events affect the operation of a rolling shutter image sensor having a global shutter period, the light events would affect the operation of any rolling shutter image sensors and global shutter image sensors.

FIG. 4A illustrates the exemplary operation of the rolling shutter image sensor on a time scale showing the relative timing of pixel row resets and readouts. As shown, the image sensor is driven in accordance with a nominal frame rate of 120 fps (i.e., 8.3 milliseconds per frame). But, instead of reading the rows of pixels of the sensor at every possible frame period, rows are read every other frame period, allowing the sensor pixels to integrate for a longer period (i.e., effectively two frame periods of the nominal frame rate). The longer integration period, referred to as the "global shutter" window, is depicted by the shaded parallelogram 402. The sensor array is sensitive during the entire 16.6-millisecond global shutter window. Thus, the shaded parallelogram 402 represents the exposure of one single frame. During the global shutter period, illumination is provided during window 404 so that all of the rows of pixels are illuminated simultaneously and the resulting image frame is substantially free of rolling shutter effects. Additional details of the rolling shutter image sensor can be found in U.S. patent application Ser. No. 16/745,154 titled "SYSTEMS AND METHODS FOR MEDICAL IMAGING USING A ROLLING SHUTTER IMAGER" filed on Jan. 16, 2020, the content of which is incorporated by reference in its entirety.

With reference to FIG. 4A, if an unintended/undesirable light event occurs, there is a 100% probability that it would produce artifacts in one or more frames. For example, any light events occurring in the time period 406 (i.e., the reset of the last row to the readout of the first row), such as Light Event 2, would undesirably illuminate all rows of the current frame, thus generating artifacts (e.g., blowout) in the current frame. As another example, any light events occurring in the parallelogram 402 outside the time period 406, such as Light Event 1, would undesirably illuminate some rows of the current frame and some rows of the adjacent previous frame, thus generating artifacts (e.g., horizontal lines) in two frames, as shown in FIG. 4B. In other words, regardless of when an unintended/undesirable light event occurs, there is a 100% probability that artifacts will appear in one or more frames. This is a significantly higher probability than a global shutter image sensor, for which artifacts only appear when the light events lines up with the exposure window (e.g., 1 out of 16.6 milliseconds).

While FIG. 4A illustrates how unintended/undesirable light events affect the operation of a rolling shutter image sensor having a global shutter period, the light events would affect the operation of any rolling shutter image sensors and global shutter image sensors as described above. Further, the unintended/undesirable light events may affect various types of frames, including white light frames and fluorescence image frames.

Method for Reducing Artifacts in an Image Frame

FIG. 5 provides an exemplary method 500 for imaging tissue of a subject using a rolling shutter imager to provide a video stream. With method 500, the image frames are generated with reduced or eliminated artifacts. Method 500 may be performed by an imaging system, such as imaging system 300 of FIG. 3, that has a rolling shutter imager, such as rolling shutter imager 302 of system 300, and a light source, such as light source 330 of system 300. In process 500, some blocks are, optionally, combined, the order of some blocks is, optionally, changed, and some blocks are, optionally, omitted. In some examples, additional steps may be performed in combination with the process 500. In some examples, subsets of the blocks are performed in separate processes—for example, blocks 502-508 and blocks 510-518 can belong to two separate processes even though they are shown together in FIG. 5. Accordingly, the operations as illustrated (and described in greater detail below) are exemplary by nature and, as such, should not be viewed as limiting.

At step 502, a plurality of the rows of pixels of the rolling shutter imager are reset. In some examples, the reset is performed via a "synchronous frame reset" functionality of the rolling shutter imager. With the synchronous frame reset functionality, charge accumulated in the plurality of rows of pixels is cleared simultaneously or within a short time period. In some examples, the plurality of rows of pixels are reset within a time period shorter than a line-by-line offset period of the rolling shutter (e.g., the time period between the start of line 1 and the start of line 2 in FIG. 4A). However, unlike the global shutter imager, readout of the plurality of rows of pixels is performed sequentially row by row with a time offset in the same manner as a rolling shutter imager. In some systems, the synchronous frame reset functionality is intended to be used in a photo camera with a flashlight to produce a single frame photo image. In method 500, however, the synchronous frame reset feature is used in a novel configuration to reduce or eliminate artifacts in image frames in a video stream, as described below.

Figure 6A:
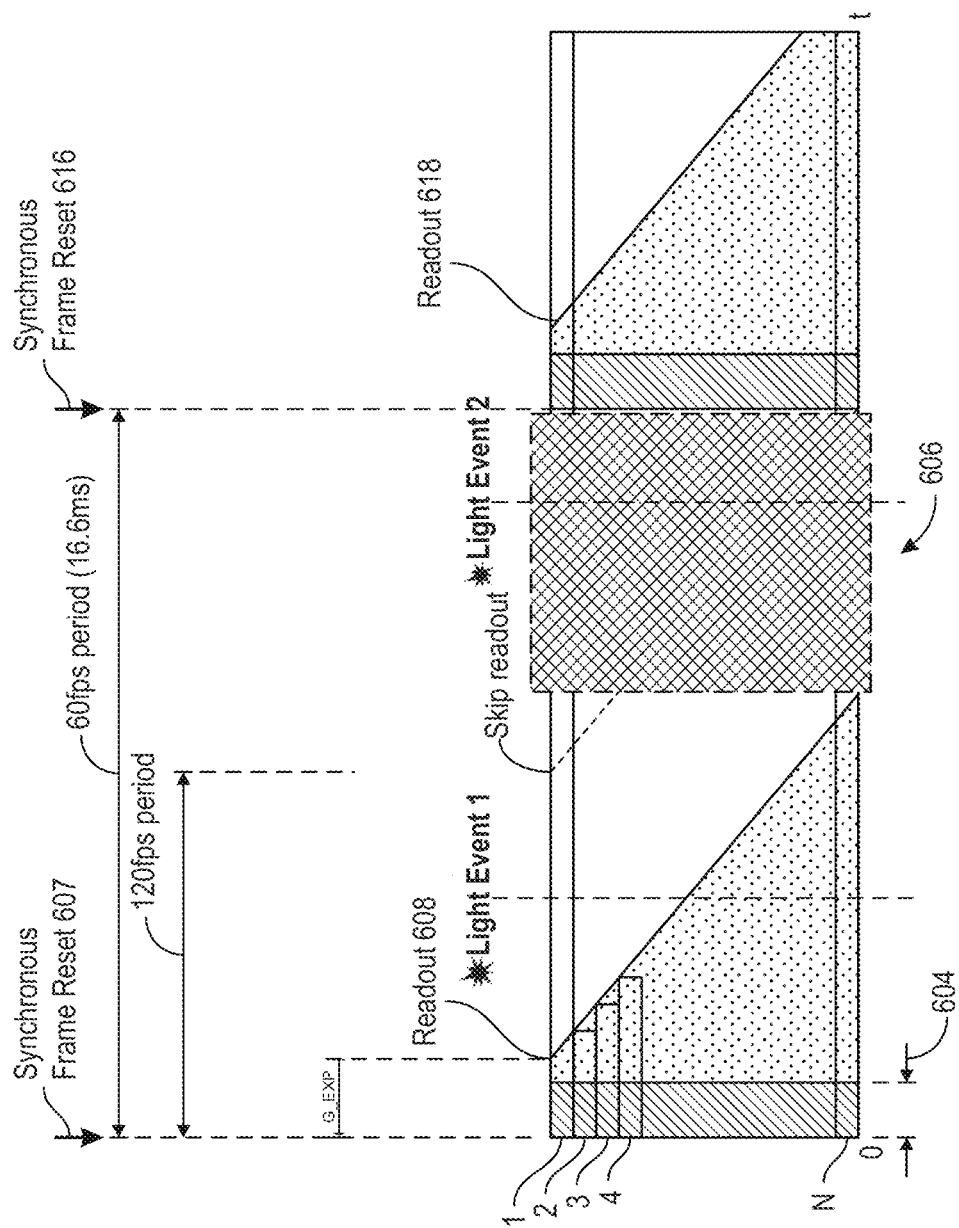
FIG. 6A is a diagram showing how artifacts can be reduced or eliminated with a rolling shutter image sensor having a "synchronous frame reset" functionality, according to some examples.

FIG. 6A illustrates a rolling shutter image sensor implementing the method 500, in accordance with some examples. FIG. 6A illustrates the exemplary operation of the rolling shutter imager on a time scale showing the relative timing of pixel row resets and readouts. Similar to the example in FIG. 4A, the image sensor is driven in accordance with a nominal frame rate of 120 fps (i.e., 8.3 milliseconds per frame), but instead of reading the rows of pixels of the sensor at every possible frame period, rows are read every other frame period. Thus, only one readout of the rows occurs during two frame periods (i.e., a 16.6-millisecond period). With reference to FIG. 6A, at time 0, all of the rows 1-N of a frame are reset via the synchronous frame reset feature at 607. Thus, all of the rows 1-N start exposure together and accumulating charges at time 0. In some examples, the reset is simultaneously or substantially simultaneously (e.g., shorter than a line-by-line offset period of the rolling shutter imager) effected across all rows.

Returning to FIG. 5, at step 504, after resetting the plurality of rows of pixels, the tissue of the subject is illuminated with an illumination light for an illumination period. With reference to FIG. 6A, after the rows 1-N of the frame are reset via the synchronous frame reset functionality at time 0, the field of view is illuminated and the rows 1-N accumulate charge from light received from the field of view during an illumination period 604. In some examples, an illuminator is controlled to provide illumination light over the illumination period; for example, a controller can control the imaging sensor and the illuminator so that they are synchronized.

At step 506, charge accumulated at the plurality of rows of pixels is sequentially read from a first row to a last row. With reference to FIG. 6A, charge accumulated at rows 1-N is sequentially read row-by-row from the first row to the last row as indicated by 608.

In some examples, the synchronous frame reset functionality provides a configurable constant parameter (also referred to as "G_EXP") that defines the time between the triggering of the synchronous frame reset and the readout of the first row. Thus, the illumination period needs to be set to be shorter than (or at most equal to) the parameter so that the readout of the first row does not occur during the illumination period and that all pixels of the frame are exposed during the entirety of the illumination period. With reference to FIG. 6A, the illumination period is set to be shorter than G_EXP and thus the readout of the first row is set to occur shortly after the illumination period. Accordingly, when the first row is read out at 608, it had been exposed during the entire illumination period 604. The rest of rows are left exposing until they are read out sequentially, as indicated by 608. While the rows are being read out, they are not illuminated (other than by unintended/undesirable light events that happen to occur). With a conventional rolling shutter, the last row would get more light than the first row because of its later readout time, but this is mitigated in FIG. 6A because all rows stop receiving light at the same time.

In some examples, after the synchronous frame reset functionality is triggered, a separate signal is needed to trigger the readout of the first row at 608. This separate signal needs to be issued at or after the end of the illumination period so that all pixels of the frame are exposed during the entirety of the illumination period before the first row is read out.

Returning to FIG. 5, at step 508, an image frame is generated from the readings of accumulated charge at the plurality of rows of pixels. With reference to FIG. 6A, an image frame is generated from the sequentially read accumulated charge at rows 1-N as indicated by 608. Optionally, the rows 1-N are then reset.

In some examples implementing the method 500, two resets occur at two different times before each image frame is generated. For example, with respect to the second frame in FIG. 6A, a first reset of the rows 1-N can occur at a first time 608 after readout of the first frame, a second reset (i.e., a synchronous frame reset) of the rows 1-N occurs at a second time 616, and the accumulated charge at rows 1-N is read at a third time 618. Between the first time 608 and the second time 616, no readout of the rows 1-N occurs. In some examples, the reset at 608 is optional.

The method 500, with its novel use of the synchronous frame reset functionality, can significantly reduce the impact of undesirable/unintended light events on the image frames. First, any light event that occurs before the synchronous frame reset time would not affect the frame. Consider Light Event 2 in FIG. 6A for example. Because Light Event 2 occurs after the readout of the first frame and before the synchronous frame reset of the second frame, it does not affect either frame. In fact, any light event that occurs in window 606 would not affect any image frame.

Furthermore, even if a light event occurs when a frame is exposed, the light event would only impact one frame. Consider Light Event 1 in FIG. 6A for example. Because Light Event 1 occurs before the synchronous frame reset of the second frame, it only affects the first frame and has no impact on the second frame, as shown in FIG. 6B. Thus, Light Event 1 and Light Event 2 would affect 1 frame in total. In contrast, in the example depicted in FIG. 4A without the synchronous frame reset functionality, Light Event 1 and Light Event 2 would affect 3 frames in total. In some examples, the synchronous frame reset feature as depicted in FIG. 6A would eliminate impactful light events by about 46%.

According to some examples, an imager may be configured for any suitable frame rate. Exemplary frame rates include at least 25 fps, at least 30 fps, at least 50 fps, at least 60 fps, at least 100 fps, at least 120 fps, at least 200 fps, and at least 240 fps. Global shutter window times and/or extended vertical blanking times are generally related to the frame rate capability of the imager, whereby faster frame rates will be associated with shorter global shutter window times and/or shorter extended vertical blanking times.

Returning to FIG. 5, at step 510, the system determines whether the image frame meets one or more criteria. As discussed above, the synchronous frame reset functionality may not eliminate the impact of all light events (e.g., Light Event 1 in FIG. 6A). Thus, step 510 can be performed to identify compromised image frames and exclude the compromised image frames from the video stream.

In some examples, step 510 comprises identifying one or more artifacts in the image frame at step 512. Exemplary techniques for identifying artifacts in the image frame are provided below.

In some examples, identifying one or more artifacts in the image frame comprises identifying a horizontal line or vertical line in the image frame. As shown in FIG. 6B, an artifact can comprise a horizontal line delineating a color change from a darker upper portion to a brighter lower portion. The color change is caused by the light event (e.g., Light Event 1 in FIG. 6A) that occurred during the sequential readout of the rows. The horizontal line may appear anywhere in the image. In an alternative example in which the sensor is rotated, the artifact line may have a different angle (e.g., vertical). In some examples, the calculation can be done with respect to a region of interest.

In some examples, a Sobel filter is used to detect lines in the image frame. The Sobel filter can be modified to focus more on the horizontal lines and/or the dark-to-bright transition. An exemplary Sobel convolution can be [1 2 3 2 1; 0 0 0 0 0; −1 −2 −3 −2 −1]. The convolution can be applied to the luminance channel of the image frame. After the Sobel convolution is applied, the Sobel image can be processed to remove all values lower than a threshold (e.g., 20 on a 8-bit y-channel) such that only positive transitions are considered and the noise floor is removed. The Sobel image can be binarized with mean value, and then the number of active pixels in a line can be counted. The system can then differentiate the active pixel counts along the y-axis. In some examples, a filter (e.g., a gaussian kernel [0.25 0.5 0.25]) can be applied, and then the minimum value and the maximum value can be determined. If the difference between the minimum value and the maximum value (i.e., the max/min slope) is above a threshold, a horizontal line is detected. It should be appreciated that other techniques for detecting lines in an image frame (e.g., using other types of filters) can be used.

In some examples, identifying one or more artifacts in the image frame comprises calculating a rate of increase from mean values of one or more previous image frames to a mean value of the image frame. Although not all light events cause a saturation of the pixels, many events can still be detected by analyzing the slope of the increase of the mean value. In some examples, a mean value of an image frame is the mean value of all pixels of the image frame. The deviation of the mean value (denoted as ΔMean) for an image frame can be then calculated as the difference of the mean values of a previous image frame and the image frame. The deviation of the ΔMean (denoted as ΔΔMean) can be then calculated as the difference between the ΔMean of the last good frame and the ΔMean of the current image frame divided by the number of frames between. If ΔΔMean is larger than a predefined threshold, the image frame can be determined to have an artifact. In some examples, the calculation can be done with respect to a region of interest. In some examples, rather than using a mean value, the system can perform the calculation using a median value or a modified median value (e.g., a median value that excludes pixels having darkness above a threshold from the calculation).

Identifying one or more artifacts in the image frame can comprise: calculating an increase from a number of saturated pixels in a previous image frame to a number of saturated pixels in the image frame. A large increase in saturated pixels from one frame to another (pre-gain) may indicate a light event. In some examples, the number of newly saturated pixels (e.g., all pixels above a certain threshold) can be detected in a frame, and the difference with the last good frame is determined. If the difference is larger than a predefined threshold, the image frame can be determined to have an artifact. In some examples, the calculation can be done with respect to a region of interest.

Identifying one or more artifacts in the image frame can be based on color information. For example, the identification can comprise evaluating a difference between at least two of a red channel, a blue channel, and a green channel of the image frame. If there is a difference among the channels (e.g., between red and one or more of the other channels) above a predefined threshold, the image frame can be determined to have an artifact. In some examples, the calculation can be done with respect to a region of interest.

Identifying one or more artifacts in the image frame can comprises: processing the image frame using a trained machine-learning algorithm, such as a trained neural network. The algorithm can be trained to receive an image frame and classify the image frame as having an artifact or not having an artifact.

Identifying one or more artifacts in the image frame can be based on pixels in the field stop region of the image frame, which normally does not receive light due to light rays being blocked by the field stop of the endoscope. During a light event, the blowout can be so significant that stray light impinging on the imager sensor (e.g., from stray reflections within the endoscope or camera) extends into the field stop region and causes an increased amount of light in the field stop region. As shown in FIG. 6B, the lower portion of the field stop region in the affected image frame appears lighter than the field stop region in the unaffected image frame, which is completely dark. Thus, if the system detects an increased amount of light in the field stop region exceeding a predefined threshold, a compromised image can be identified.

In some examples, a filter (e.g., a Sobel filter) can be configured to identify line(s) in the field stop region to identify a compromised image. For example, the filter can be configured to identify longer lines in the field stop region of the frame near the top or bottom of the frame, and shorter lines in the field stop region near the middle of the frame.

The above-described techniques for detecting artifacts can be optionally combined, ordered, and omitted in step 512 of the method 500. For example, detecting horizontal or vertical lines may only be applied to an image frame captured using a rolling shutter imager, while the other techniques can be applied to an image frame captured using either a rolling shutter imager or a global shutter imager. In some examples, additional steps may be performed in combination with the techniques. Accordingly, the above-described techniques are exemplary by nature and, as such, should not be viewed as limiting.

Returning to FIG. 5, in some examples, step 510 comprises placing the frame in a buffer of a predefined size at step 514. A sequence of frames captured by the imager can be accumulated in the buffer. Each image accumulated in the buffer can be associated with a respective score. The score is indicative of how likely the image is compromised by a light event. The score can be calculated based on detected artifacts (or the lack thereof) in the image frame and, in some examples, can be calculated using any combination of the techniques described herein (e.g., horizontal lines, mean values of pixels, etc.).

Figure 7:
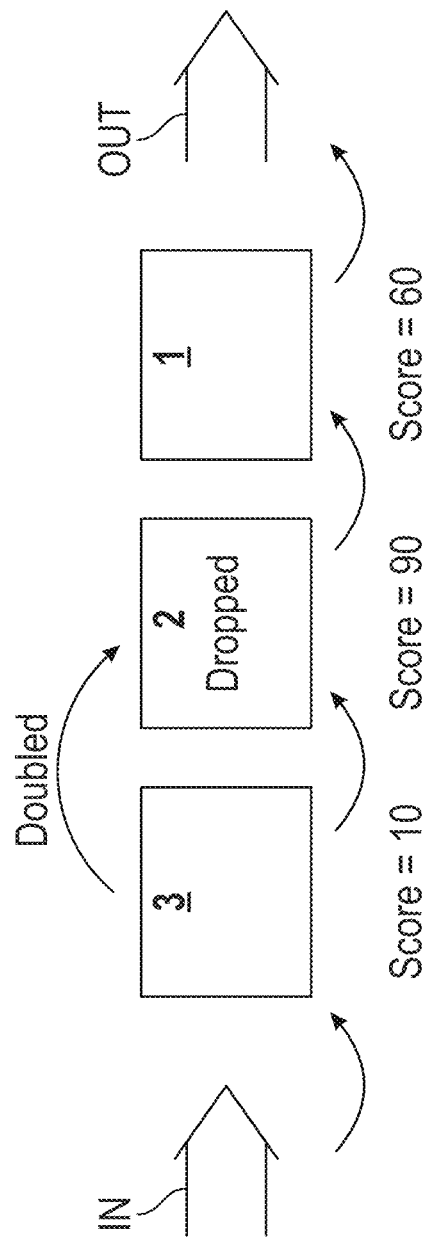
FIG. 7 illustrates an exemplary N-frame buffer wherein N equals three, according to some examples.

FIG. 7 illustrates an exemplary N-frame buffer wherein N equals three. As shown, a sequence of three image frames is accumulated in the buffer. The three image frames are associated with scores 60, 90, and 10, respectively, wherein a higher score indicates a higher likelihood that the image is compromised. The scores of the image frames in the buffer can be compared and, based on the comparison, an image frame is identified as the image to exclude from the video stream. In the depicted example, the system is configured to drop the worst image from the sequence of image frames. Accordingly, frame 2 is dropped from the sequence of image frames because it has the worst score.

Advantageously, the N-frame buffer can reduce false-positives and maintain a low drop count. In the depicted example in FIG. 7, if there is no buffer and the system is configured to drop every image having a score over a threshold of 50, the system would have dropped frame 1. However, frame 1 may be a false positive that should not have been dropped—for example, frame 1 may have a high mean value of the pixels comparing to the previous frames because the instrument moved and detected brighter pixels when there is no light event. Further, if the system is configured not to drop consecutive images, the system would then drop frame 1 but keep frame 2, even though frame 2 has a much higher score and is actually caused by a real light event. Using the buffer, the system correctly drops frame 2 and keeps frame 1.

In the depicted example, the system is configured to drop at most one image frame from the buffer. In some examples, the system is able to drop more image frames. The maximum number of image frames that can be dropped may depend on the frame rate of the camera, the frame rate of the video stream, the aggressiveness of the algorithm (described below), or a combination thereof.

In some examples, after an image frame is dropped from the sequence of image frames, the system identifies another image frame to replace the dropped image frame in the sequence. In some examples, the replacement image frame is selected from the sequence of image frames based on the scores. In the depicted example in FIG. 7, frame 3 is selected because it has the best score. Accordingly, an updated sequence of image frames (i.e., frame 1, frame 3, frame 3) can be added to the video stream.

The buffer can introduce a latency in the system. Rather than immediately adding each image frame to the video stream as soon as the image frame is generated, multiple frames are accumulated in the buffer and evaluated together before the first frame is added to the video stream. The size of the buffer determines the amount of latency incurred—the larger the buffer, the longer the latency. In some examples, if the frame rate of the camera is higher than the frame rate of the video stream, the latency may not be perceptible. In other words, the system has a higher latency tolerance. Thus, the buffer size can be determined based on the latency tolerance of the system. In some examples, the buffer size is between 3 frames and 6 frames.

In some examples, the buffer has a size of 1 such that only one image frame is stored in memory to replace the next frame if the next frame is compromised.

Returning to FIG. 5, at step 516, in accordance with a determination that the image frame does not meet the one or more criteria, the image frame is added to the video stream; at step 518, in accordance with a determination that the image frame meets the one or more criteria, the image frame is discarded. If the image frame is discarded, it can be replaced by another image frame (e.g., the last good frame, the best frame in the buffer, a repaired frame). In some examples, the number of frames that can be consecutively discarded is limited to a pre-defined threshold or based on the aggressiveness of the algorithm as described below. In some examples, a discarded image frame does not influence the auto gain exposure ("AGC") algorithm to prevent a negative flash; alternatively, the discarded image causes the AGC algorithm to be adjusted by a smaller weight factor.

While the steps in the method 500 are described with respect to a rolling shutter imager, the techniques in method 500 can be used for either a rolling shutter imager or a global shutter imager. For example, steps 510-518 can be used to evaluate image frames captured by a global shutter imager to detect compromised image frames and eliminate them from the video stream.

The aggressiveness or sensitivity of the method 500 can be adjusted automatically or manually. Specifically, any of the steps and any of the parameters in method 500 can be automatically adjusted, such as one or more thresholds for identifying an artifact in the image frame, a size of an image buffer, a maximum number of image frames droppable from the image buffer, a maximum number of consecutive image frames droppable from the image buffer, or any combination thereof. In some examples, the aggressiveness of the method can be dynamically adjusted upon detection of activation of a surgical energy device (e.g., a laser unit, an RF probe) and/or upon detection of a light event (e.g., via a photodiode). In these cases, the system may automatically activate any combination of the steps in method 500 or increase their aggressiveness or sensitivity to capture compromised image frames. On the other hand, absent detecting activation of a surgical energy device or a light event, the system may automatically deactivate any combination of the steps in method 500 or reduce their aggressiveness or sensitivity.

For example, one way to adjust the sensitivity of step 514 is to automatically increase the size of the buffer in response to detecting a light event. In other words, the system accepts a higher latency but improves the ability to identify compromised images. Absent a light event, the system can automatically decrease the size of the buffer or bypass it completely (i.e., setting the size to 0). As another example, the system can automatically activate any of the techniques in step 512 or increase their sensitivity in response to detecting a light event and do the opposite absent a light event.

Detecting activation of the surgical energy device can comprise receiving a signal from a surgical energy device (e.g., a laser unit, an RF probe). For example, the signal can be a signal from a control unit of the energy device that a holmium laser is, has been, or will be ouputted by the unit. In some examples, the energy device is commanded by a foot pedal. Thus, a hardware component (e.g., a pressure sensor) can be coupled to the foot pedal and configured to send a signal whenever the foot pedal is pressed.

Detecting activation of the surgical energy device can comprise detecting an increase in power consumption of the surgical energy device. For example, the detection can be performed by a remote clamp mounted on the power cable to determine an increase in power consumption.

Detecting the light event can comprise receiving a signal from a photodetector mounted in the imager. The photodetector can be positioned in the camera head (e.g., mounted to the prism) or clamped to the camera body (e.g., on or near the entrance window of the camera body) to capture stray light or reflected light in the camera body. In some examples, the unintended/undesired light event can comprise infrared that does not exist in the desired imaging spectrum of the camera. Thus, a filter (e.g., an infrared filter) can be placed in front of the photodetector to ensure that the photodetector detects only the unintended/undesired light event. In some examples, the system is configured to treat any light detected by the photodetector that does not correspond to the imager's light source as an unintended/undesirable light event. In some examples, whether an image frame is compromised can be directly determined by comparing the timing of the detected light event against the reset and readout times of the frames, as shown in FIG. 6A and demonstrated in FIG. 6B. If a light event is detected, the system can automatically identify the affected frame(s) and flag those frames (e.g., by adjusting the scores associated with the frames).

Detecting activation of the surgical energy device can comprise receiving acoustic signals from the surgical energy device. For example, an acoustic microphone can be used to detect acoustic signals indicative of a light event, such as the safety tones or distinct chatter generated by a laser during firing. A machine-learning algorithm can be trained to recognize the acoustic signals.

In some examples, motion of the imager can be detected and used to adjust the sensitivity of the steps in method 500. Motion of the imager can be detected via an inertial measurement unit of the imager or via image tracking. If the imager is moving, the sensitivity can be reduced to avoid the detection of false positives.

While some of the examples includes a rolling shutter sensor having horizontal lines that are read from the top row to the bottom row, it should be appreciated that the techniques described herein can be applied to imaging sensors having different orientations, layouts, and readout orders, without departing from the spirit of the invention.

Reducing Artifacts Using a Shutter

In some examples, a shutter can be used to reduce or eliminate artifacts caused by unintended/undesirable light events. The shutter can be: a liquid crystal shutter, a mechanical shutter, a DLP mirror, or an electromechanical shutter. When activated, the shutter can block a substantial portion of light from the imaging path. When deactivated, the shutter allows a substantial portion of light to pass through.

With reference to FIG. 6A, a shutter (e.g., an LC shutter) can be configured to activate at the end of the illumination period 604 to block a substantial portion of light from the imaging path. Accordingly, any light event occurring during the sequential readout at 608, such as Light Event 1, would not impact the image frame. In some examples, the shutter can be configured to transition from a deactivated state (i.e., allowing a substantial portion of light to pass through) to an activated state (i.e., blocking a substantial portion of the light) in a short amount of time. Thus, the rows of pixels are reset simultaneously or substantially simultaneously via synchronous frame reset at 607 to start accumulating charge, and also stop receiving light simultaneously or substantially simultaneously via the shutter at the end of the illumination period.

The shutter is deactivated before the synchronous frame reset 607. In some examples, the LC shutter takes longer to transition from an activated state to a deactivated state. Thus, the deactivation may be triggered to occur at an early enough time such that the LC shutter is completely deactivated at 607.

A shutter with pulse width control can also be used to reduce impact of unintended/undesirable light events, as illustrated in FIGS. 8A-B. In FIGS. 8A-B, a global shutter imager is driven in accordance with a frame rate of 60 fps (i.e., 16.6 milliseconds per frame) and has an exposure window of 1 millisecond per frame period.

As shown in FIG. 8A, under standard operation, if a light event happens to line up with the 1 ms exposure window, the sensor may be exposed to the light event during much of the 1 ms exposure window, which can cause significant artifact in the image frame.

In FIG. 8B, rather than setting a continuous 1-ms exposure window during the 16.6-ms frame period, the sensor is configured to be exposed during the entirety of the 16.6-ms frame period to accumulate charge. A shutter with pulse width control is configured to deactivate, for n times (n=5 in FIG. 8B), one n-th of the actual desired 1-ms exposure period (200 us in FIG. 8B) or less to permit light to pass through the shutter. The image can be generated based on the accumulated charge after the n-th deactivation. In other words, the shutter controls the light such that the light is permitted to reach the sensor only for the desired exposure time or less in aggregate, even though the sensor is exposed during the entire 16.6-ms frame period. As shown in FIG. 8B, if a light event happens to occur in the frame period, the impact is less severe because it can only impact a portion of the 1-ms total exposure time.

The n deactivations of LC shutters can be spaced apart at least by the desired exposure time (e.g., 1 ms in the depicted example). In some examples, the value of n can be adjusted. For example, n can be automatically increased to reduce the impact of a light event if the system determines that the light event is occurring, has occurred, or is likely to occur using the techniques described herein.

While FIG. 8B illustrates the use of a shutter in a global shutter imager, it should be appreciated that the shutter can be used in a similar manner in other types of imagers such as a rolling shutter imager. Further, the implementation can be achieved using density modulation of the shutter, in some examples.

Instead of activating and deactivating a shutter, multiple periods of charge accumulation for an image frame can be achieved using a global shutter sensor that allows charge accumulation to be pulsed. For example, the sensor allows charge accumulation to be active or inactive based on an external control signal. Charge accumulation can be deactivated, for example, using bypass circuit(s).

The shutter can also be configured to operate as a standalone device without communication with the imager. The shutter can be installed in the imaging path. For example, the shutter can be a replacement coupler or a drop-in accessory at an endoscope's eyepiece. The shutter can be powered by its own power source (e.g., internal battery, solar cell).

Figure 9:
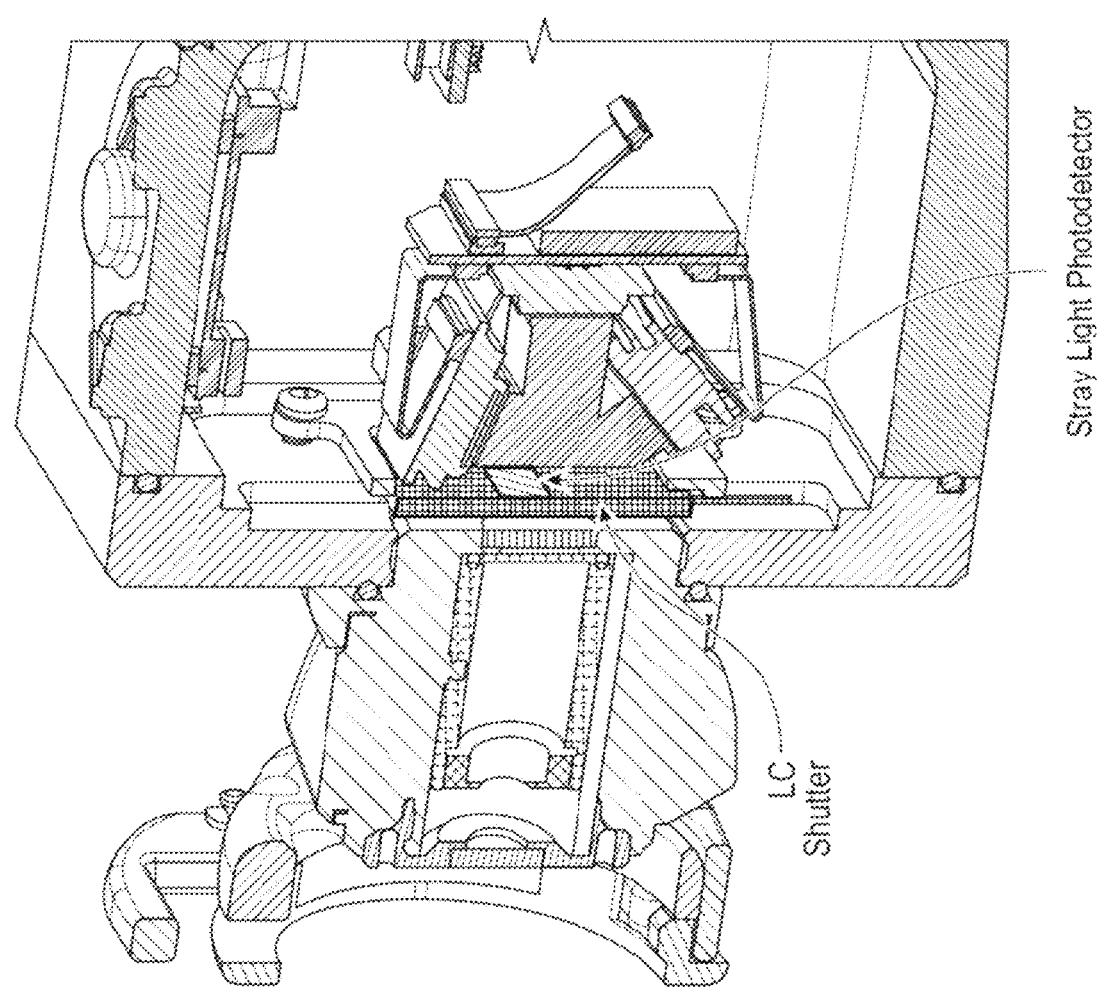
FIG. 9 illustrates an exemplary shutter for blocking unintended/undesirable light events in the imaging path of an imager, according to some examples.

In particular, the shutter device can have a photodiode for detecting light events. The photodiode may be located at an external surface of an imager prism, as shown in FIG. 9. For example, the photodiode can be sensitive to IR to detect unintended/undesirable light events (e.g., laser events may contains some IR) but not sensitive to the light source of the imager or to other desired light for imaging (e.g., emitted fluorescence light). When a light event is detected, the LC shutter closes within a very short period (e.g., 500 us to 1 ms), sparing the image sensor from the majority of the contamination. As soon as the detected light event is over, the LC shutter is configured to open just as quickly as it closed. Laser light events are typically shorter than 1 ms. Thus, if camera exposures are reasonably larger than that, not much negative effect will be perceived. If the exposure is short, the frame may appear darker rather than a blown out frame.

While the photodiode is shown to be mounted to the LC shutter in FIG. 9, the photodiode can be mounted in other locations of the system. In some examples, a stray light photodiode can be placed on the LC shutter on the image/sensor side. It can be mounted facing toward the sensor on the LC shutter (or mating components) outside the incoming image beam clear aperture (i.e. beam/image height at this location in Z). The sensor/prism assembly does not capture all incoming light and some of that light is reflected back out of the prism assembly. The photodiode can capture this stray light that is leaving the prism/sensor assembly.

In some examples, a stray light photodiode can be mounted to the LC shutter on the object/endoscope side. It can be mounted facing toward the endoscope on the LC shutter (or mating components) outside the incoming image beam clear aperture (i.e. beam/image height at this location in Z). The prism assembly does not capture all incoming light, and the LC shutter does not transmit all incoming light. Reflections at these interfaces cause reflected stray light to leave the system and reflect off optical elements upstream (e.g. endoscope exit window) to be directed back toward the sensor, but outside the original imaging beam. The photodiode can capture some of this secondary reflection of light off the upstream optics.

In some examples, a stray light photodiode can be mounted to the prism entrance surface. The photodiode can be mounted to the prism glass entrance surface outside the incoming image beam clear aperture (i.e. beam/image height at this location in Z), facing (a) toward the endoscope or (b) toward the sensors. A photodiode facing toward the endoscope can capture the secondary reflection (with the primary reflection being from the sensor/prism assembly out of the system) off the LC shutter or other upstream optical elements, or capture stray light from the incoming beam that is generated from interfaces of the upstream optical elements. A photodiode facing toward the sensors can capture the primary reflection from the sensor/prism assembly that is leaving the prism assembly.

In some examples, a photodiode can be mounted to the prism entrance surface with a pickoff optic or diffractive optical element (DOE). Such a configuration is similar to a photodiode facing toward the endoscope described above but with a pick off optic or DOE incorporated to enable incoming beam sampling (with no reliance on stray light/internal system reflections).

In some examples, a photodiode can be mounted with a dichroic mirror (beamsplitter)—the photodiode is mounted in the free space that exists around the coupler optics, the shutter, the sensor/prism assembly, and the image beam (i.e., the remaining air space within the camera housing that is not occupied by those components). A dichroic mirror is positioned in the imaging beam's optical path to reflect at least some of the light event's IR content to the photodiode while passing white light through to the sensor assembly.

In some examples, a photodiode can be mounted in the free space described above facing toward the entrance window.

In some examples, a photodiode can be mounted in the free space described above adjacent to the entrance window coupled with a pickoff optic.

In some examples, upon detection of a light event, the system can compare the timing of the detected light event against the reset and readout times of the frames, as shown in FIG. 6A and demonstrated in FIG. 6B. This way, the system can automatically identify the affected frame(s), which in turn can be dropped and replaced. For example, the affected frames can be flagged (e.g., by adjusting the scores associated with the frames) for further processing.

While some of the examples are described with reference to an LC shutter, it should be appreciated by one of ordinary skill in the art that other types of shutters can be used, such as a mechanical shutter, a DLP mirror, an electromechanical shutter, an optical shutter, etc. in examples of the present disclosure.

Figure 10:
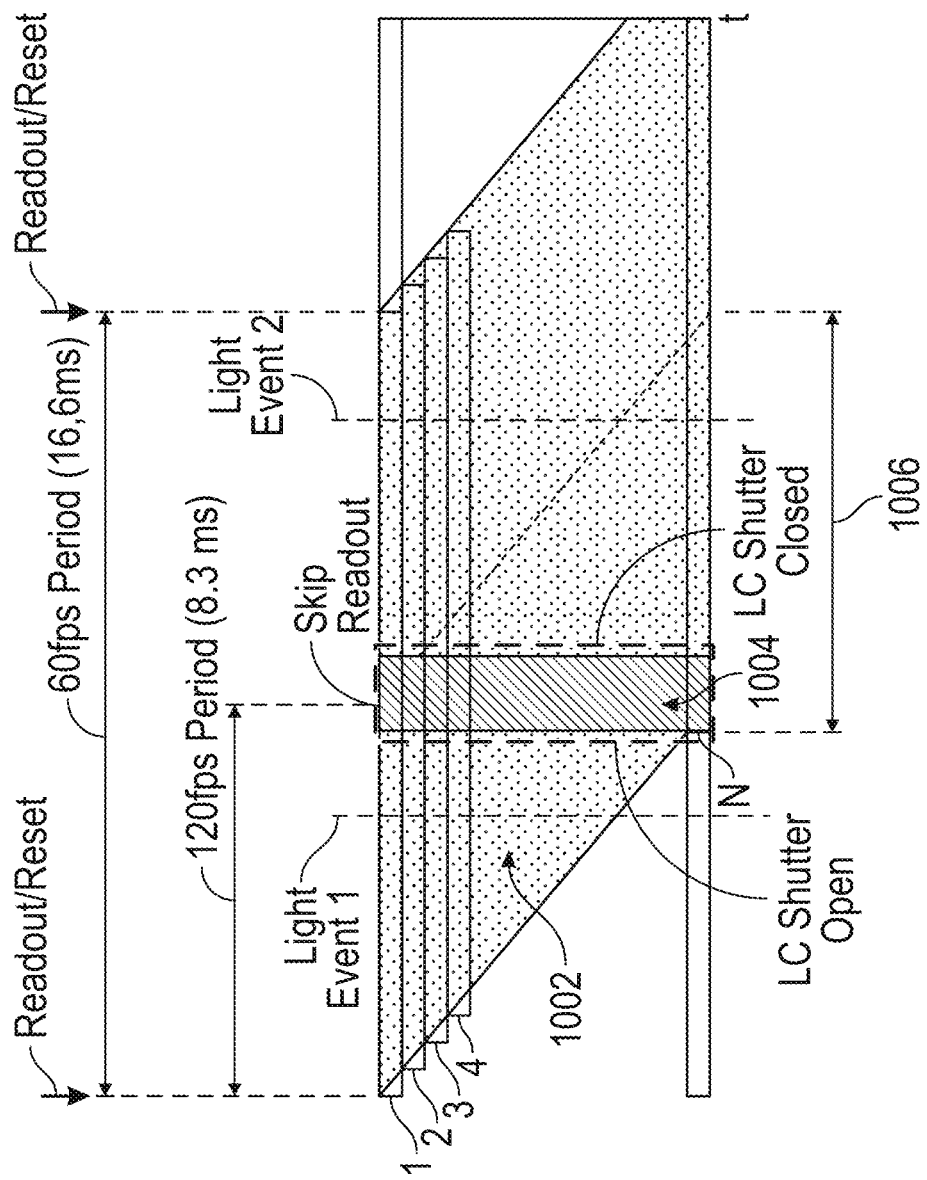
FIG. 10 illustrates another exemplary operation of a rolling shutter image sensor for reducing artifacts in an image frame, in accordance with some examples.

FIG. 10 illustrates another exemplary operation of a rolling shutter image sensor for reducing artifacts in an image frame, in accordance with some examples. FIG. 10 illustrates the operation on a time scale showing the relative timing of pixel row rests and readouts.

The example in FIG. 10 is similar to that of FIG. 4A in that the rows are read every other frame period rather than every period. This way, the system allows the sensor pixels to integrate for a longer period (i.e., effectively two frame periods of the nominal frame rate). The shaded parallelogram 1002 represents the exposure of one single frame when the image sensor is driven in accordance with a nominal frame rate of 120 fps (i.e., 8.3 milliseconds per frame). The sensor array is sensitive during the entire 16.6-millisecond window depicted by the shaded parallelogram 1002. In particular, during the time period 1006 between the reset of the last row N and the readout of the first row, all or substantially all of the rows of the imager can be simultaneously exposed, effectively creating a global shutter window in which illumination light can be provided such that rolling shutter effects are prevented.

In the depicted example in FIG. 10, the illumination period 1004 starts at the beginning of window 1006. This is in contrast with the example in FIG. 4A, where the illumination period 404 starts during, but not right at the beginning of the window 406. Further, the system opens a liquid crystal shutter to expose pixels in the sensor array to the illumination during the illumination period. As shown, the liquid crystal shutter starts transitioning from a closed state to an open state slightly before the start of the illumination period 1004. This way, the liquid crystal shutter can be fully transitioned into the open state when the illumination period 1004 starts, thus preventing chromatic effects that may occur while the shutter is transitioning from a closed state to an open state.

In some examples, the liquid crystal shutter starts transitioning from the open state to the closed state slightly after the end of the illumination period 1004. This way, the transitioning of the liquid crystal shutter would not affect any portion of the illumination period, again preventing chromatic effects that may occur while the shutter is transitioning between states. In alternative examples, the liquid crystal shutter can close before or at the end of the illumination period, because the closing speed of the liquid crystal shutter is much faster than the opening speed and thus the chromatic effects may be less pronounced.

In one exemplary implementation, the liquid crystal shutter takes about 1.3 ms to fully open and 50 us to fully close. Further, it is determined that the shutter is chromatically stable after about 800 us on the opening side. Thus, the shutter can be configured to start transitioning to the open state 800 us in advance of the illumination period. The transitioning to the closed state can start simultaneously with the end of the illumination period as there is no effect once the light source turns off. Another reason for transitioning to the closed state after the end of the illumination period is that the system could operate the shutter without knowledge of the desired light pulse and let automatic gain control in the camera make up the difference. It should be appreciated that the asymmetric opening and closing times of the liquid crystal shutter are based on how it is constructed and a shutter could be constructed in the opposite way to make the opening time faster and the closing time slower, and the timing for opening and closing the shutter relative to the illumination period can be adjusted accordingly.

In some examples, rather than starting the illumination period at the beginning of window 1006, the illumination period can start at another time during the window 1006. The entirety of the illumination period falls within the window 1006. Further, the liquid crystal shutter is configured to open and close based on the illumination period, as described above. Since the camera and the light source are varying exposure times based on the length of 1006, the system can either fix the start time and vary the end time of the illumination period or fix the end time and vary the start time of the illumination period.

In some examples, a timer device can be used to set the liquid crystal shutter open time and close time based on a vertical sync pulse (either the vsync of the frame acquisition or the vsync of the light source). In some examples, the system can adjust the open time and/or the close time of the liquid crystal shutter based on the imaging scene (e.g., brightness, modality). In some examples, the system can use a boost converter to generate a relatively high voltage (e.g. 24V) inside the camera head from a lower operating voltage, in order to drive the liquid crystal shutter with the relatively high voltage.

While some of the examples are described with reference to an endoscope, it should be appreciated by one of ordinary skill in the art that the techniques described herein in can be used in any imaging systems, including flexible and/or chip-on-tip scopes in which the image sensor is located at the distal end of a scope, such as a flexible digital ureteroscope.

The foregoing description, for the purpose of explanation, has been described with reference to specific examples. However, the illustrative discussions above are not intended to be exhaustive or to limit the invention to the precise forms disclosed. For the purpose of clarity and a concise description, features are described herein as part of the same or separate examples; however, it will be appreciated that the scope of the disclosure includes examples having combinations of all or some of the features described. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

What is claimed is:

1. A method of imaging tissue of a subject using a rolling shutter imager to provide a video stream, the method comprising:
   sequentially resetting a plurality of rows of pixels of the rolling shutter imager from a first row to a last row;
   transitioning a liquid crystal shutter from a closed state to an open state;
   after the liquid crystal shutter is transitioned into the open state and after resetting the last row, illuminating the tissue of the subject with an illumination light for an illumination period to accumulate charge at the plurality of rows of pixels, and
   after the illumination period ends, sequentially reading the accumulated charge at the rows of pixels from the first row to the last row;
   generating an image frame from the sequentially read accumulated charge at the plurality of rows of pixels; and
   adding the image frame to the video stream.

2. The method of claim 1, wherein the illumination period is at least a portion of the time period between when the last row is reset and when the first row is read.

3. The method of claim 2, wherein the illumination period starts when the last row is reset.

4. The method of claim 1, wherein the plurality of rows of pixels is exposed for the same period of time to generate the image.

5. The method of claim 1, further comprising: after the end of the illumination period, starting transitioning the liquid crystal shutter from the open state to the closed state.

6. The method of claim 1, further comprising: at the end of the illumination period, starting transitioning the liquid crystal shutter from the open state to the closed state.

7. The method of claim 1, further comprising: before the end of the illumination period, starting transitioning the liquid crystal shutter from the open state to the closed state.

8. The method of claim 1, wherein the liquid crystal shutter is opened or closed using a timer device based on a vertical sync pulse.

9. The method of claim 1, wherein the liquid crystal shutter is opened or closed based on one or more characteristics of an imaged scene.

10. The method of claim 9, wherein the one or more characteristics of the imaged scene comprise brightness and/or modality of the imaged scene.

11. The method of claim 1, wherein the illumination light is generated by at least one LED.

12. The method of claim 1, wherein the rolling shutter imager is part of an endoscopic imager.

13. The method of claim 1, wherein the rolling shutter imager is part of a flexible and/or chip-on-tip scope.

14. A system of imaging tissue of a subject to provide a video stream, the system comprising:
   an illumination source; and an imaging apparatus that comprises a rolling shutter imager, the imaging apparatus being configured for:
- sequentially resetting a plurality of rows of pixels of the rolling shutter imager from a first row to a last row;
- transitioning a liquid crystal shutter from a closed state to an open state;
- after the liquid crystal shutter is transitioned into the open state and after resetting the last row, illuminating the tissue of the subject with the illumination source for an illumination period to accumulate charge at the plurality of rows of pixels, and
- after the illumination period ends, sequentially reading the accumulated charge at the rows of pixels from the first row to the last row;
- generating an image frame from the sequentially read accumulated charge at the plurality of rows of pixels; and
- adding the image frame to the video stream.

15. The system of claim 14, wherein the illumination period is at least a portion of the time period between when the last row is reset and when the first row is read.

16. The system of claim 15, wherein the illumination period starts when the last row is reset.

17. The system of claim 14, wherein the plurality of rows of pixels is exposed for the same period of time to generate the image.

18. The system of claim 14, wherein the imaging apparatus is further configured for: after the end of the illumination period, starting transitioning the liquid crystal shutter from the open state to the closed state.

19. The system of claim 14, wherein the imaging apparatus is further configured for: at the end of the illumination period, starting transitioning the liquid crystal shutter from the open state to the closed state.

20. The system of claim 14, wherein the imaging apparatus is further configured for: before the end of the illumination period, starting transitioning the liquid crystal shutter from the open state to the closed state.

21. The system of claim 14, wherein the liquid crystal shutter is opened or closed using a timer device based on a vertical sync pulse.

22. The system of claim 14, wherein the liquid crystal shutter is opened or closed based on one or more characteristics of an imaged scene.

23. The system of claim 22, wherein the one or more characteristics of the imaged scene comprise brightness and/or modality of the imaged scene.

24. The system of claim 14, wherein the illumination source comprises at least one LED.

25. The system of claim 14, wherein the rolling shutter imager is part of an endoscopic imager.

26. The system of claim 14, wherein the rolling shutter imager is part of a flexible and/or chip-on-tip scope.

* * * * *